(12) United States Patent
Heneghan et al.

(10) Patent No.: US 11,191,466 B1
(45) Date of Patent: Dec. 7, 2021

(54) DETERMINING MENTAL HEALTH AND COGNITIVE STATE THROUGH PHYSIOLOGICAL AND OTHER NON-INVASIVELY OBTAINED DATA

(71) Applicant: Fitbit, Inc., San Francisco, CA (US)

(72) Inventors: Conor Joseph Heneghan, Campbell, CA (US); Alexander Statan, Oakland, CA (US); Jonathan David Charlesworth, San Francisco, CA (US)

(73) Assignee: Fitbit Inc., San Francisco, CA (US)

( * ) Notice: Subject to any disclaimer, the term of this patent is extended or adjusted under 35 U.S.C. 154(b) by 0 days.

(21) Appl. No.: 16/457,582

(22) Filed: Jun. 28, 2019

(51) Int. Cl.
| | |
|---|---|
| *A61B 5/16* | (2006.01) |
| *A61B 5/0205* | (2006.01) |
| *A61B 5/00* | (2006.01) |
| *A61B 5/11* | (2006.01) |
| *A61B 5/145* | (2006.01) |
| *A61B 5/01* | (2006.01) |
| *G16H 50/30* | (2018.01) |
| *A61B 5/1455* | (2006.01) |
| *A61B 5/024* | (2006.01) |

(52) U.S. Cl.
CPC ............... *A61B 5/165* (2013.01); *A61B 5/01* (2013.01); *A61B 5/02055* (2013.01); *A61B 5/1118* (2013.01); *A61B 5/14546* (2013.01); *A61B 5/14551* (2013.01); *A61B 5/162* (2013.01); *A61B 5/4815* (2013.01); *A61B 5/6802* (2013.01); *A61B 5/7267* (2013.01); *A61B 5/742* (2013.01); *G16H 50/30* (2018.01); *A61B 5/02416* (2013.01)

(58) Field of Classification Search
CPC ....... A61B 5/165; A61B 5/01; A61B 5/02055; A61B 5/1118; A61B 5/14546; A61B 5/14551; A61B 5/162; A61B 5/4815; A61B 5/6802; A61B 5/7267; A61B 5/742; A61B 5/02416; G16H 50/30
USPC .......................................................... 600/301
See application file for complete search history.

(56) References Cited

U.S. PATENT DOCUMENTS

| | | | |
|---|---|---|---|
| 10,020,076 B1 * | 7/2018 | Anumalasetty | ........ G16H 10/60 |
| 10,213,145 B1 * | 2/2019 | McNair | .............. A61B 5/02416 |
| 2008/0071181 A1 * | 3/2008 | Stabler | .................. A61B 5/352 |
| | | | 600/509 |
| 2008/0214903 A1 * | 9/2008 | Orbach | .................. A61B 5/165 |
| | | | 600/301 |

(Continued)

*Primary Examiner* — Carl H Layno
*Assistant Examiner* — Michael J Lau
(74) *Attorney, Agent, or Firm* — Dority & Manning, P.A.

(57) ABSTRACT

Physiological variables, metrics, biomarkers, and other data points can be used, in connection with a non-invasive wearable device, to screen for, and predict, mental health issues and cognitive states. In addition to metrics such as heart rate, sleep data, activity level, gamification data, and the like, information such as text message and email data, as well as vocal data obtained through a phone and/or a microphone, may be analyzed, provided user authorization. Applying predictive modeling, one or more of the monitored metrics can be correlated with mental states and disorders. Identified patterns can be used to update the predictive models, such as via machine learning-trained models, as well as to update individual event predictions. Information about the mental state predictions, and updates thereto, can be surfaced to the user accordingly.

19 Claims, 6 Drawing Sheets

(56) References Cited

U.S. PATENT DOCUMENTS

| | | | | |
|---|---|---|---|---|
| 2010/0292545 A1* | 11/2010 | Berka | A61B 5/168 | 600/301 |
| 2011/0224498 A1* | 9/2011 | Banet | A61B 5/6824 | 600/300 |
| 2012/0068876 A1* | 3/2012 | Bangera | G06F 3/017 | 342/27 |
| 2012/0135804 A1* | 5/2012 | Bender | A61B 5/165 | 463/36 |
| 2014/0023999 A1* | 1/2014 | Greder | A61B 5/16 | 434/236 |
| 2014/0051047 A1* | 2/2014 | Bender | G16H 40/67 | 434/238 |
| 2014/0243608 A1* | 8/2014 | Hunt | A61B 5/168 | 600/300 |
| 2014/0316230 A1* | 10/2014 | Denison | A61B 5/165 | 600/383 |
| 2015/0031003 A1* | 1/2015 | Kullok | A61B 5/4088 | 434/236 |
| 2015/0088542 A1* | 3/2015 | Balassanian | A61B 5/165 | 705/2 |
| 2015/0332012 A1* | 11/2015 | Edelson | A61B 5/7275 | 705/2 |
| 2016/0081607 A1* | 3/2016 | el Kaliouby | A61B 5/0022 | 434/236 |
| 2016/0144278 A1* | 5/2016 | el Kaliouby | G16H 40/63 | 463/36 |
| 2016/0262680 A1* | 9/2016 | Martucci | A61B 5/4088 | |
| 2017/0021279 A1* | 1/2017 | Kim | A63F 13/00 | |
| 2017/0071545 A1* | 3/2017 | Ritscher | A61B 5/02405 | |
| 2017/0098122 A1* | 4/2017 | el Kaliouby | G16H 50/30 | |
| 2017/0100032 A1* | 4/2017 | Zakariaie | A61B 5/163 | |
| 2017/0119297 A1* | 5/2017 | Flax | A61B 5/4812 | |
| 2017/0156657 A1* | 6/2017 | Flax | A61B 5/4809 | |
| 2017/0223413 A1* | 8/2017 | Kozloski | H04N 21/462 | |
| 2017/0337438 A1* | 11/2017 | el Kaliouby, Jr. | A61B 5/165 | |
| 2018/0032944 A1* | 2/2018 | Sarvana | G06Q 10/063114 | |
| 2018/0050171 A1* | 2/2018 | Tabert | A61B 5/7455 | |
| 2018/0104439 A1* | 4/2018 | Tzvieli | A61B 5/0816 | |
| 2019/0000384 A1* | 1/2019 | Gupta | A61B 5/6831 | |
| 2019/0015751 A1* | 1/2019 | Kahn, II | A61B 5/168 | |
| 2019/0101977 A1* | 4/2019 | Armstrong-Muntner | G06F 3/017 | |
| 2019/0110726 A1* | 4/2019 | Chatterjee | A61B 5/4884 | |
| 2019/0113973 A1* | 4/2019 | Coleman | G06F 3/015 | |
| 2019/0125255 A1* | 5/2019 | Pradeep | A61B 5/4836 | |

\* cited by examiner

DETERMINING MENTAL HEALTH AND COGNITIVE STATE THROUGH PHYSIOLOGICAL AND OTHER NON-INVASIVELY OBTAINED DATA

BACKGROUND

Recent advances in technology, including those available through consumer devices, have provided for corresponding advances in health detection and monitoring. In the meantime, wearable electronic devices have gained popularity among consumers. In order to determine user activities, a wearable electronic device collects activity data and runs computations on that data. More particularly, the wearable electronic devices may monitor or track users' activities using a variety of sensors and help the users maintain healthy lifestyles. Wearable electronic devices such as smartwatches and fitness band trackers may track metrics related to particular activities, such as a step count metric for running and walking activities. For example, devices such as these are able to determine information relating to the pulse or motion of a person wearing the device. Other metrics that may be tracked by a wearable electronic device include metrics related to sleep. Typically, a wearable electronic device will contain an interface for the user to request or provide certain data.

It is well-documented that cases of mental disorders such as depression are on the rise, and it is suspected that there are many cases which are undiagnosed, although there is no commercially-available state marker such as a blood test or blood pressure test for making the diagnosis. At best, a relatively-lengthy computer game may test cognitive ability or a psychological state can be estimated on a computing device, but the computing device must be a laptop or even a smartphone, and the related data collections are invasive and limited, not the least of which being chronologically. One known diagnostic method involves looking at activity data within a very limited, campus-type population setting in conjunction with the content of text/short message service ("SMS") messages, which, absent authorization or "opting-in," can intrude on the users' privacy. Vocal analysis has been conducted in an attempt to diagnose a bipolar mental state, but such would require an extended analytical period. There remains, however, a need to screen cognitive states and mental health condition in a regular and non-burdensome way.

BRIEF DESCRIPTION OF THE DRAWINGS

Various embodiments in accordance with the present disclosure will be described with reference to the drawings, in which.

DETAILED DESCRIPTION

Figure 1A:
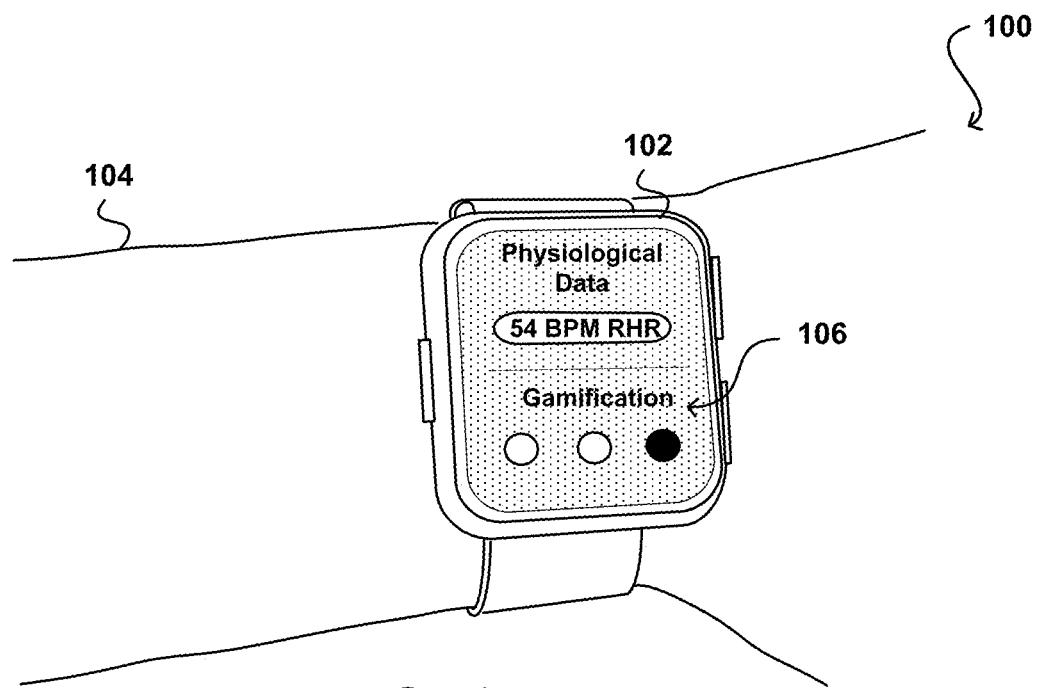
FIGS. 1A and 1B illustrate an example monitoring device that can be used to obtain, analyze, and deliver user mental and other health information in accordance with various embodiments.

In the following description, various illustrative embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiments being described.

For various reasons, it can be desirable for a person, including a medical patient, to track and analyze his or her mental state, including cognitive ability, in an automated and non-invasive fashion. It may be desired even more so that such tracking be performed with minimal intervention required. An advantage of developing an automated system lies in the fact that the tracking of factors relating to mental state can serve as a general health indicator, as significant deviations in the analyzed metrics may be indicative of underlying health issues. Performing the measurements automatically can remove opportunity for user error, such as by inputting incorrect information or inputting information inconsistently.

Approaches in accordance with various embodiments provide for health screening and monitoring, and, in particular, relate to the automated tracking and analysis of mental state information, including cognition. Various amounts of objective data points in one or more sets, including that non-invasively obtained through a worn monitoring device measuring physiological data and through fast-play gamification-type activities, are associated and correlated, through predictive models and identified biomarkers, to deliver statuses, insights, and guidance regarding the user's current mental or cognitive state and how to potentially improve it, even within a given day or for a desired timeframe. In addition to insights for building higher mental acuity, the present systems and methods can predict cognitive state and mental maladies from various data points and patterns found therein, including diagnosing potential degeneration. It should be noted well that, while the terms "mental state" or "mental health" are used throughout the present disclosure, such is merely for convenience, and those terms are not to be construed as limiting and encompass any state, condition, or disorder which could affect or otherwise relate to mood, emotions, thinking, cognition, behavior, and/or psychological well-being.

As will be seen, the predictive models and determinations can be of a self-monitoring and non-burdensome nature. Capturing physiological data and multiple elements of cognition, including, but by no means limited to, multitasking ability and reaction/response time, impulsiveness, risk-averse status, and vigilance. As is known, these elements can be sensitive to factors such as sleep quality and caffeine intake, rendering routine capture very useful. Through presentation of insights and guidance hereunder, a user can see the impact of how things like exercising, napping, eating, stress, or drinking coffee impact his or her cognitive functioning.

In some embodiments, historical information can be obtained for a user that can contain information such as medical background and existing conditions. This information can assist in the screening for events, such as the start and stop of, for example, depressive disorder episodes. In order to improve the accuracy of those predictions, one or more of the designated physiological data or metrics can be monitored for the user and correlated with the user's mental state. In addition, in comparing and presenting the cognitive insights and guidance hereunder, the user's data can be compared to baseline data for a general population.

Various illustrative embodiments capture and consider objective physiological data non-invasively obtained through wearable monitoring device sensors and logged, such as activity, sleep, heart rate ("HR"), and the like. These physiological data variables and metrics can further include, by way of but some examples, comparable biomarkers such as the user's resting heart rate ("RHR") and/or other HR-derived data, blood oxygen concentration ($SpO_2$) level, heart rate variability ("HRV"), sleep duration and quality, exercise levels, weight, hemoglobin, and water concentration, as well as concentration of oils/lipids/collagen on the skin, among other options. The present systems and methods may additionally or alternatively utilize electrodermal measurements as well as information from other types of devices, such as from a chest band or an electrocardiogram ("ECG") patch. Textual analysis of emails and text messages, as well as voice analysis of phone calls, provided the user has consented to all of such in accordance with applicable laws and regulations, may be factored in the analyses hereunder as well, as can data obtained via gamification efforts. Even specifics and conditions of a user's interaction with his or her wearable monitoring device, smartphone, and/or other devices can be captured and analyzed, such as how often the device is checked and how hard buttons are being pushed.

Additional information can be taken into account as well, such as may include age, health, medication, changes in exercise or diet, or other information that may impact the user's mental state. Information from the user can be input as well, as may relate to symptoms or other health aspects discussed and suggested herein. In some embodiments, the user information will be applied to make an initial prediction, and the predictive modeling will use this as a starting point to attempt to improve outputted predictions. In other embodiments, the physiological data will be automatically collected and used to screen for, and predict, mental state, and the user-provided information will provide accuracy information which can be used to refine or retrain the predictive model, such as where machine learning is used to analyze the data. That said, and as will be seen, the types of captured data points and metrics comprising a data set for a given user are, by design, virtually unlimited.

In an illustrative embodiment, patterns of heart rate, sleep, and physical activity are analyzed by one or more predictive model algorithms, which can vary depending on factors such as system configuration and what physiological objective data is collected and analyzed. In particular, potential categories of objective, physiological data points may include the most predictive ones such as: resting heart rate; heart rate variability; mean steps per day; active minutes; mean sleep schedule, such as when, on average, the user goes to bed and when he or she awakens; length of time before falling asleep, once in bed; number of sleep interruptions; and sleep stages, including amount of "deep" sleep. Three conditions of particular focus in some embodiments are as follows: a high resting heart rate, a low activity level (determined by time spent in specific heart rate zones, such as fat-burning and cardiovascular), and inconsistent, or high variation in, sleep duration. It will be apparent that, for purposes of tracking the sleep-oriented metrics, the user would most likely need to wear a smartwatch or some other monitoring device capable of capturing the needed sleep data for determining length, quality, stages, and the like.

In the interest of computing speed and delivering results as quickly as possible to the user, one approach is to calculate the data on the user's worn monitoring device and transmit the results to a remote server. With such a configuration, the user could see results essentially immediately in some embodiments, or at least within a reasonable time, via engaging software applications and/or interfaces as discussed herein. Another approach is to capture all physiological metrics and raw gaming data, with a remote server doing the requisite calculations. Data can be compressed prior to transmission over a network such as the internet (commonly referred to "the cloud"). The capture in some embodiments may be user-initiated or triggered, as by buttons or touch-screen areas designated for starting and stopping the capture.

The categories and types of metrics may be customized, and the data collected passively, with the user not required to perform any action in order for the data to be transmitted to the cloud or other network. One or more of the health-related metrics can be monitored over time to determine patterns or cycles of variation in the metrics, which can be correlated with mental state. In particular, analysis of how much variation there is within the various categories of inputs will prove helpful in performing the mental health and cognitive screening herein. This information can then be used to update predictive models, as well as to update individual event predictions based at least in part upon the current values of those metrics for the user. Information about the predictions, and updates to the predictions, can be surfaced to the user, which can assist with planning around life events, such as, to name but one example, by recommending a bedtime in light of an upcoming important test or job interview.

Notably, the obtained information can also be used to deliver mental state statuses and insights to the user. For example, lower time spent in high heart-rate zone can be a biomarker for a depressive state, and sleep data can be analyzed and a determination can be made that the user is sleeping poorly. The user can then be provided with information about determinations made, as well as various suggestions for potential remedial actions. Data, be it physiological or gamification-obtained, can also be analyzed to provide other insights as to various symptoms or states when correlations are identified, such as to convey to a user that, when exercising regularly, he or she will experience an improved mental state. Of course, it is advisable that the cognitive data be updated through games and tests, which aid in identifying areas where the user's cognitive performance varies. Further, it is envisioned that user-provided medical history and food logging can be included in the data points and the analysis thereof.

It is certainly possible to focus on specific measurements correlating, or otherwise relevant, to a particular mental state or cognitive function. With regard to impulsiveness, for example, a user desiring to develop better habits and/or lose weight or the like, if the user is very impulsive on a given day, he or she likely would make less healthy choices, such as consuming food which is on the less healthy side. The monitoring herein can provide insight in this regard, as, for example, it could be determined that the user is more impulsive when his or her sleep schedule is irregular at best, which impacts food choices as well as energy for exercise and fitness efforts. Behavior modification approaches can be applied in shaping the related interfacing and coaching. Gamification in some embodiments can assist users in building habits beneficial to cognitive function, with the goal of making a user the best he or she can be from a mental standpoint. The insights and guidance, generated from the analysis of collected data points, can be used to select a subset of games to play based on the known data.

A predetermined period for collection of the physiological data and other metrics can comprise one week in some illustrative embodiments, but it is envisioned that any sort of timeframe can be utilized, subject to local and remote data storage and processing capabilities. For example, a user's data over the previous month could be analyzed. Screening algorithms are applied to the captured metrics and data points, which can culminate in requests for additional data and user participation in one or more suggested programs. Through machine learning implementations, the systems and methods herein can "learn" from the tracking and acquire a knowledge platform for automated coaching and advising.

The data points and analysis can be applied to generate a personalized program for preventing cognitive impairment and/or degeneration associated with aging, and for allowing users of all ages to be more cognitively-ready and optimizing mental acuity, for example by tracking progress and getting mentally ready for a critical test at school. In this vein, features such as tracking and automated reminders permit a user to better schedule life events such as meetings and bedtimes.

The monitoring device interface, as well as messaging and other ways in which any interactions with the user are made, may be changed and vary depending on the predictions and analyses made by the systems and methods illustrated herein, including if a user is predicted to currently be in a depressed episode. Various other functions can be implemented within the various embodiments as well as discussed and suggested elsewhere herein.

As noted, in various embodiments, the present systems and methods can be implemented on one or more electronic monitoring devices able to automatically measure or determine aspects of the health or wellbeing of the wearer. The user can wear or utilize a variety of these computing devices, including, but not limited to, wearable devices such as smartwatches and fitness trackers, which have one or more sensors for capturing one or more instances of physiological data points. "Smartwatch" use, in particular, permits a user to answer less cognitive-oriented questions, during gamification efforts or otherwise, while automatically obtaining noteworthy data such as heart rate and sleep information that can be applied in determining a subset of the questions to pose to the user. One example embodiment 100 of such a monitoring device smartwatch 102 is illustrated in FIG. 1A, although other devices such as "smart" or network-connected fitness trackers and bands, watches, rings, earbuds, phones, clothing, and the like can be utilized as well within the scope of the various embodiments. Further embodiments can include, at least in part, a desktop, laptop, or tablet computer setting, including where a user provides heart rate data through electronic communication another device such as a chest strap. In this example embodiment 100, the user can wear the smartwatch 102 on an arm 104 and view health-related and/or gamification information on a display screen 106 of the watch. In many embodiments the display 106 will be a touch sensitive display allowing the wearing user to input or receive information relevant to his or her mental state and health as discussed herein.

Figure 1B:
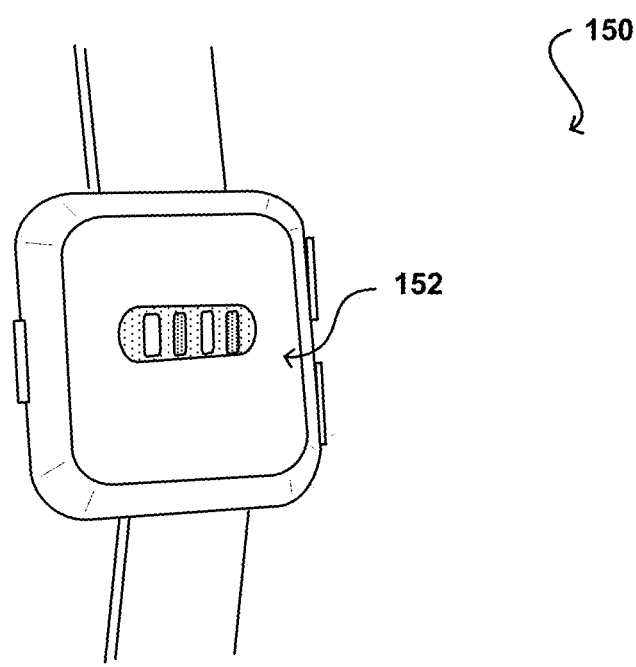

The monitoring device 102 may include various sensors, such as motion and temperature sensors, which can be used to measure or detect information about the user. The sensors in some illustrative embodiments are non-invasive and do not require that any sort of instrumentation be introduced into the wearing user's body. In one embodiment, a user interface can provide the capability for the user to enter designated data types. The watch 102 can also include an optical measurement sub-system 152, such as is illustrated in the example back view 150 of the smartwatch 102 illustrated in FIG. 1B. In this example, the optical measurement sub-system 152 includes at least one optical emitter and at least one optical detector or receiver. The emitter can emit light of one or more wavelengths that can be reflected from the surface of the user's skin, or diffusely reflected after traveling, under the surface, and detected by at least one of the receivers. Such an optical assembly can enable the monitoring device smartwatch 102 to measure various types of information during times in which the user is wearing the monitoring device 102.

Figure 1C:
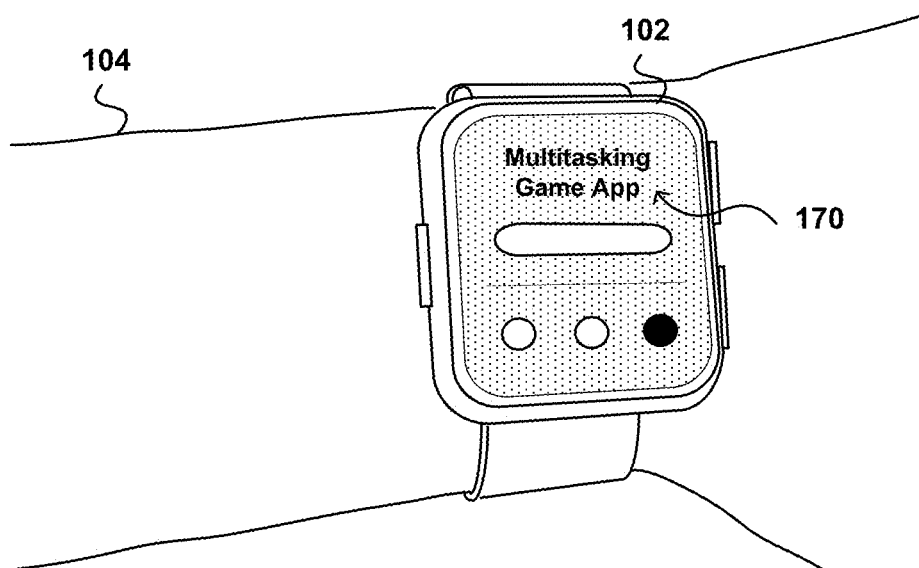
FIGS. 1C and 1D illustrate an example monitoring device that can be used to obtain data through gamification concepts in accordance with various embodiments.
Figure 1D:
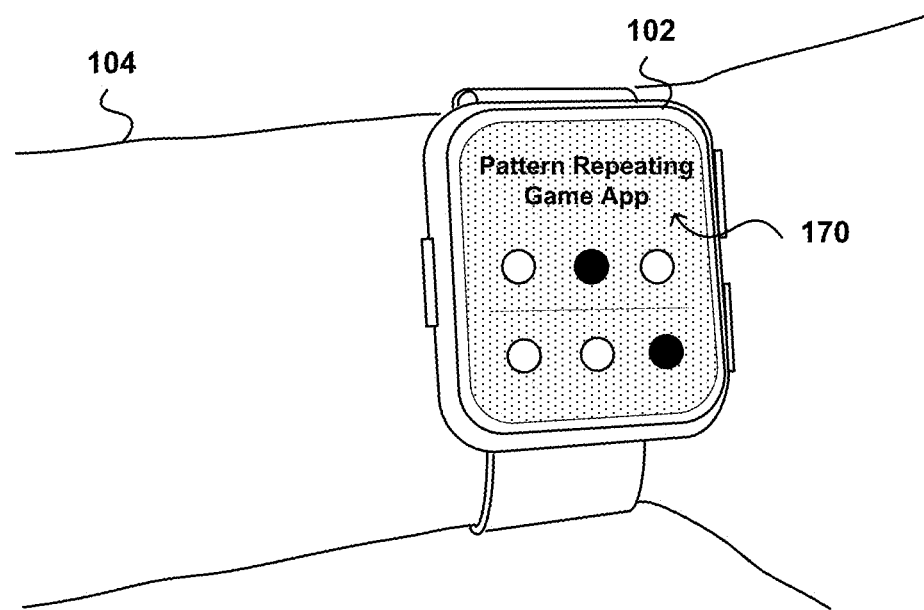

Gamification is the application of game design elements and game principles in non-game contexts, to encourage participation, engagement, and loyalty. With the goal of building upon notions such as detecting cognitive (non-emotional) state (i.e., a mental state as to how well one currently can think or how well one's brain is working), software apps for the user can relate to areas such as problem solving ability, executive functioning, and attention readiness and serve to collect metrics and data points relating thereto. As discussed in further detail below, and illustrated in FIGS. 1C and 1D, it is possible to apply such gamification concepts through a wearable monitoring device 102, for example, along the lines of the illustrative devices discussed herein, executing cognitive game-type apps 170 to assist with a quick and valid measurement of a mental or cognitive state. This reduces barriers to gaining the sort of data necessary to conduct a meaningful analysis of mental state, as a user can more frequently gather data points and have such an analysis performed on a regular basis, even multiple times in a given day, which allows relationships to be determined, such as mental state when caffeinated, how performance is based on sleep and/or food consumed, and how much stress the user is under. And the selection of games can be made based on short time analytical periods and only require a minimal amount of user time, such as two minutes for a round of a game. Further, game performances could be stored such that, once a user has played a certain game, he or she would not need to play the game again in some embodiments, in order to obtain a current mental state status determination.

In one embodiment, the user can wear a monitoring device 102 containing an optical measurement sub-system photoplethysmogram ("PPG") component and an accelerometer. The PPG can obtain volumetric measurements by illuminating the skin, such as by using an emitter on a side of the watch proximate to the wearer's wrist, and measuring a change in absorption of the light over time. The frequency of these changes can be representative of the heart rate or pulse of the user. Because these measurements can be susceptible to motion effects, it may be preferable in at least some embodiments to attempt to determine the RHR of the user. This may be accomplished at night, while the user is sleeping, for example, although other periods of low activity (or even periods that are activity-independent) can be used as well within the scope of the various embodiments. The monitoring device 102 can determine the heart rate by detecting peaks in the optical signal. In some cases, there may be no clear peaks such that a heart rate cannot be reliably detected, as may be due to excessive motion. For monitoring devices 102 including an accelerometer, inertial sensor, or other such sensor or component, periods of excessive movement can be determined and then excluded from analysis. In other illustrative embodiments, the data for these periods may still be utilized, but with the motion effects accounted for in the analysis. A sensor such as an accelerometer can also be used to determine the overall sleeping period (e.g., from 11 p.m. to 7 a.m.). An estimate of the user's RHR can then be calculated. In one embodiment, a histogram of heart rate values overnight can be generated. A specified measure, such as the tenth percentile of this histogram, can then be taken as a representative value of RHR. The RHR values can be determined in other ways as well, such as by only using time segments where the user has been still for at least a minimum period of time, such as at least five minutes, and the optical signal as a sufficiently high signal-to-noise ratio. A RHR value, once determined, can be used to characterize the overall day for that subject.

Figure 2A:
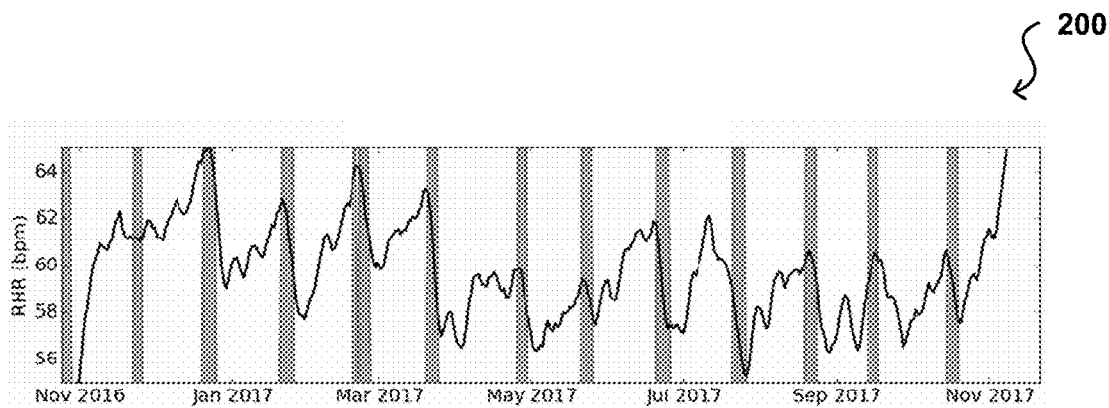
FIGS. 2A and 2B illustrate example plots of obtained heart rate data over time that can be utilized in accordance with various embodiments.
Figure 2B:
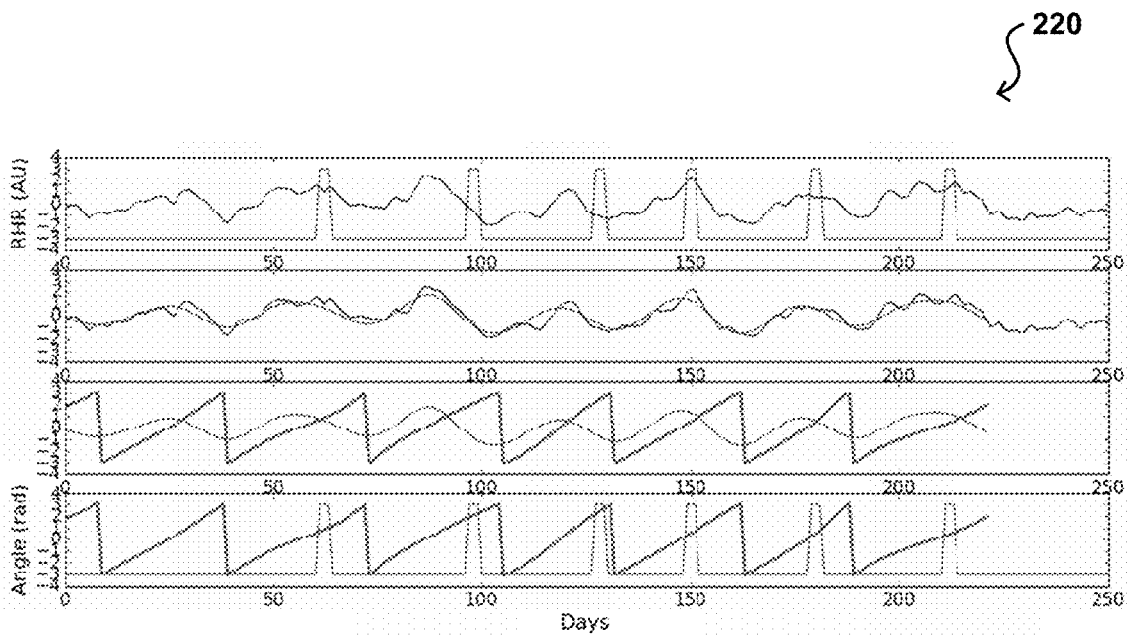

The user's history of daily resting heart rates can be collected over time, with a plot 200 of such data being illustrated in FIG. 2A. The illustrated plot 200 shows the RHR for an individual over a one-year period. FIG. 2B illustrates a set of plots 220 that can be generated in accordance with various embodiments. In this example, the top plot includes the variations in normalized RHR over a course of approximately five time cycles. As illustrated, RHR will vary over the course of time, but has distinct peaks and valleys which can correlate in at least some aspects to the mental health of the user. The top plot in FIG. 2B illustrates times of user-indicated stress as peaks in a substantially binary plot. In the second plot from the top, a filter (such as a bandpass FIR filter) is applied to the RHR data to produce a smoother RHR curve, which reduces some of the higher frequency noise in the signal. As illustrated, the filtered curve demonstrates clear peaks and valleys correlated to mental state. In the third plot from the top, the instantaneous phase of the RHR data is shown. In the bottom blot of FIG. 2B, the phase of RHR can be correlated with the points of stress. With enough data, the RHR phase can be used to improve predictions as to mental health conditions, including depressed states.

With regard to the predictive model element incorporated by the present systems and methods, in an autoregressive moving average ("ARMA") model of the RHR, the RHR is modeled as a combination of sinusoidal frequencies. Given a set of historical data, optimum values for the coefficients $w_0$ can be determined. These coefficients can then be used to predict the future RHR. An alternative embodiment of the system can use HRV metrics in place of, or in addition to, the RHR.

The wearable monitoring device 102 can calculate heart rate and movement data, although, in some embodiments, the monitoring device 102 can capture and transmit that data to a separate computing device for analysis, among other options. The monitoring device 102 in some embodiments can send the data to a local computing device, such as by using a Bluetooth signal to send the data to a smartphone which can synchronize the data with a remote database server. In embodiments where the monitoring device 102 has network connectivity, such as through Wi-Fi or a cellular network connection, the monitoring device 102 might synchronize the data to a database server without an intermediate computing device. The data can then be analyzed, such as by using a prediction and recording algorithm. The output of the algorithm can be fed back to an application ("an app") executing on the user's phone or monitoring device 102, among other such options. In some embodiments, the app can present a calendar view or other interface showing historical data, such as may correspond to the user's mental state, and indicate predicted times or dates during which depressive state or other symptoms are likely to be encountered.

At least some of the physiological or other health data can come from other devices as well. For example, a user might wear a "smart" ring capable of providing accurate heart rate information, a wrist temperature sensor that measures both skin and ambient temperature, an oral temperature sensor, or earbuds configured to provide accurate body temperature information. This information can be received and then used with other available data to attempt to generate more accurate results. For example, temperature data from earbuds alone might be used for the tracking at hand, or temperature data from earbuds, a smart ring, and a monitoring device 102 can all be analyzed together, once synchronized in time, in order to remove any temperature variations that are due to external factors, as temperature readings on the wrist may be more susceptible to changes in ambient temperature, etc. The results can be averaged or otherwise collated, or if two of the three readings are consistent with variation but the third is not, then data from the third device can be removed from consideration over the time of variation. Data from other external devices can be used as well within the scope of the various embodiments. For another example, if data is available from blood testing machinery, urine analysis devices, etc., then other information about hormone levels or body chemistry can be used as well in predicting various states and time points. Data such as temperature can be obtained from a number of other types of devices as well, such as may include smart clothing, bed sheets, wearables, and the like. Optical devices for measuring body characteristics, such as chemicals in the skin, through diffuse reflectance spectroscopy, photo-acoustic effects, optical coherence tomography, diffuse optical tomography, time-gated spectroscopy, or spatial frequency domain imaging can be used as well within the scope of the various embodiments. Different aspects of the human body will have different patterns, and these can be learned and applied to the available data to make as accurate a prediction as possible. As discussed herein, machine learning can be used to attempt to improve the accuracy of the pattern recognition and classifications over time.

Returning to gamification, it should be noted that the selection of, and even the versions of, the gaming apps 170 can differ and be customized, depending on the type of user device and storage space and computing limitations thereof; the number of graphical elements displayed may differ between, say, desktop monitors and worn monitoring devices 102, while the user movements necessitated may also differ (i.e., movement and clicking of a mouse, as opposed to one or more swipes on a smartwatch). A high-resolution screen will permit more game information to be displayed. In doing so for a tablet or smartwatch, for example, portions of a touchscreen are predetermined as user input areas, where pixels are responsive to touch. Of course, some games requiring a larger display area may simply not be suitable for a small screen such as that found on a typical smartwatch or even a mobile phone.

Different games may be presented to different users, depending on their respective histories and sensitivities with regard to sleep, physical activity, stress, and prior cognitive analyses. In other words, historical data and predicted mental state, be it general or user-specific, can inform the selection of the cognitive games and when they are to be played. In particular, any number of game models can be applied as part of a risk assessment test, to determine an inflection or turning point in mental state. Certain games and tasks may be designed to be sensitive to sleep, and games and tasks can be built to be sensitive to user stress. Other games and models directed to task-switching may measure multitasking ability. Some games may be offered to test an area or sensitivity in which the system or method is least confident.

Based on the user's history or prior game performance over a predetermined period, a baseline cognitive performance level can be established, without the user having participated in any sort of game or other self-test for a given time period, such as a day. For example, if the user has played a particular cognition game ten times, the results can provide a predictive model as to how the user's brain responds to his or her activities in the areas of sleep and physical activity. That predictive model can be applied to provide a predictor of mental state and recommend areas for potential cognitive performance improvement. And, in this vein, based on the mental state prediction, the user can be directed to one or more subsets of specific games which calculate data (e.g., multitasking ability) most likely to vary the user's cognitive functioning.

It can be helpful if the cognition-oriented gaming apps involve concepts familiar to users, such as matching patterns and sequences, as well as familiar graphical elements, such as different types of fruit, for example. In the context of a pattern repeating game, the patterns may grow increasingly difficult. Various game and testing concepts, including those which may be known in the video game and psychological testing arts, can be applied. By way of more specific example, a game directed to the metric of impulsiveness involves a balloon displayed such that it appears to be filling with air. The user will input some sort of currency (be it real or imaginary) during the filling process and, if he or she does not "cash out" before the balloon virtually pops, the user loses the currency. Users who are sleep-sensitive will typically not perform well with regard to determining when that balloon is about to pop. Of course, similar game elements faithful to this model can be employed to measure impulsiveness, without the use of a balloon. A similar, representative game can be performed using a real or virtual deck of cards. For the user, these "press your luck" sorts of games will be fun and entertaining, with an adrenaline rush provided.

Among mental states and other health issues, the present systems and methods can be applied to screen for and predict depressive disorder ("depression"), which can fluctuate and entail short or long-term episodes, as well as episodes of other conditions such as seasonal affective disorder. Again, it is likely that many cases of mild or crippling depression are undiagnosed, and there remains no commercially-available, accessible means for making the diagnosis, and the systems and methods herein can assist in accurately forming a preliminary or tentative screening for depression, without the need for subjective input from the user. Of particular benefit is the ability to perform a diagnosis for previously-undiagnosed people. Gaming apps oriented to user motivation can assist in this regard. For certain mental states where a user might be borderline depressed, the systems and methods may increase monitoring device 102 sensitivity and/or collect additional data in the interest of making a more accurate diagnosis. The look, style, messaging, or interaction with the monitoring device may be adjusted based on a determined or predicted depressive state.

It is well known that many types of testing can yield a "false positive," which is a result incorrectly indicating that a particular condition or attribute is present. Additional steps may be taken with the subject systems and methods and their predictive model algorithms to eliminate false positives, such as requesting or obtaining additional data and/or analyzing user metrics as tracked over a longer period of time. For example, more data as to sleep disturbances may be sought, and the subject monitoring device's sensitivity automatically adjusted. The additional data may entail further capture and analyses of physiological data such as sleep stages, heart rate variability, and even minute-by-minute heart rates, as well as monitoring of biochemical markers through blood chemistry. Some data points may be user-entered, including indicators of one or more personal events relevant to depression or another mental health disorder. Embodiments can allow for further user input through an app running on the monitoring device 102 or other mobile device. For such input, the user could select icons (e.g., emojis) which might reflect stress, illness, and mood, among other such options. Obtaining more details could require added storage capacity, either locally on a device or remotely over a network, and a user to affirmatively "opt-in." And it should be noted that even a false positive can indicate a user who is nevertheless potentially at risk of a condition and worthy of further monitoring, for example by virtue of a higher-than-expected resting heart rate or widely-fluctuating bed times. Indeed, a grouping of false positive cases can identify lifestyle characteristics which may be of value to other users.

A probability score may be calculated with regard to the likelihood that a given user is at risk for a malady, including depression, and applied to update the current status of the user's mental state. If, for example, the user's probability score is close to 0 or 1, then established metrics and timeframes for a base level of testing may suffice for the preliminary diagnosis. But, say, if a given user's score falls in the middle, such as between 0.2 and 0.8, then the further data collection and analyses may be warranted. To assist in the data collection efforts, an automated notification may be customized and transmitted to the identified user to remind him or her to wear the monitoring device 102 as much as possible, including during sleep, and requesting access to the user's device microphone, text message data, calendar, camera, etc. As noted, the user may opt-in to a specific monitoring program, which might generate a signal showing when the user is more and/or less at risk based on the user's habits.

In this vein of procuring additional data to avoid a false positive, a psychological evaluation instrument, such as the Patient Health Questionnaire-9 ("PHQ-9"), may be taken by the user and validated by a professional to aid in making the preliminary diagnosis by scoring each of the nine relevant criteria in the Diagnostic and Statistical Manual of Mental Disorders, 4th Edition, the familiar "DSM-IV." The PHQ-9 is known for having extremely high accuracy in diagnosing a current depressed psychological state. If the obtained sensor data and automated algorithms herein result in an initial screen indicating possible depression, as a follow-up step in some illustrative embodiments, the user may be sent the PHQ-9 form for completion, although not all questions in the PHQ-9 need be asked of a user, be it one "at-risk" or otherwise. An analysis of a completed PHQ-9 form may result in the user being sent a suggestion to consult a medical professional and possibly authorize additional monitoring through the user's monitoring device 102 data, smartphone data, microphone data, brain wave data, and/or other sources of data input which could pinpoint, say, the beginning of a depressed state episode. The analysis can result in users being categorized or groups by, say, any PHQ factors. Predictive modeling and analyses hereunder may flag when a user is identified as being in a "down" phase, even if not clinically depressed, and automatically intervene if, say, a suicide risk threshold is met (for example, PHQ-15 level). These analyses could be configured to pinpoint particular times of concern for the user such as weekends, around paydays, after a sporting contest, etc.

The additional data can be used for lifestyle customizations, such as automatically generating one or more of exercise, sleep, and diet programs for the user, as well as used by medical practitioners to monitor the dosage, efficacy, etc. of treatments and medications, be they prescribed or over-the-counter. Wearable device healthcare programs and employee-sponsored wellness programs are but a couple of program settings where such data capture and analyses would prove beneficial to highly-engaged parties and yield mental health predictions, among other deliverables.

Generally speaking, via machine learning techniques, one or more systems may be trained on a set of metrics, physiological data and/or otherwise, for a particular user or a general population. Physiological data and other metrics are then captured from the particular user and analyzed by the trained systems to determine relationships between that user's metrics, and then a mental state status and/or guidance can be pushed to the user.

A machine learning system using a convolutional neural network ("CNN"), for example, can be designed to extract HR metrics during sleep. The CNN can be trained on a data set, such as, for example, during different sleep stages, and the optimal sleep stage can be determined to predict mental health-related events. A long short-term memory neural network ("LSTM"), hidden Markov model, or other time series model can be designed to predict mental state events based on previous history, this model can also take into account any of the appropriate variables discussed herein. Multiple LSTM models can be trained to predict different factors relating to mental health in various embodiments. Moreover, it is certainly within the scope of the present disclosure to apply feedforward, recurrent, radial basis function, modular, and/or self-organizing neural networks.

Turning to algorithms and other specifics of mental state predictive modeling via heart rate, HRV can be calculated in some embodiments by first determining the time intervals between successive heartbeats. The detected PPG peaks or troughs can be used to form a peak-to-peak ("PP") time series. The variability of the PP series can reflect the control of the heart, and, to a much smaller extent, the influence of the autonomic nervous system on the blood vessel compliance. Main influences on the PP interval can include the parasympathetic nervous system (whose activation tends to slow the heart rate and hence lengthen PPG), and the sympathetic nervous system (whose activation tends to speed up the heart and shorten PP interval). The parasympathetic ("PS") and sympathetic systems can operate on slightly different time scales. Specifically, the PS system may operate on a very short time scale and affect the next beat; the sympathetic system is mediated through acetylcholine and takes multiple beats to take effect. One way to capture this difference is to take the spectral density of the PP series using a technique simply called HRV analysis. The higher-frequency components of the spectrum will reflect the parasympathetic activation since they correspond to short time scales, while lower frequency components reflect both parasympathetic and sympathetic effects.

In one illustrative embodiment, HRV parameters such as low frequency ("LF") and high frequency ("HF") power can be calculated. One convention is to define a HF band between 0.15 Hz and 0.4 Hz, as well as a LF band between 0.05 Hz and 0.15 Hz in the power spectral density estimate. Further discussion of approaches for defining these frequencies can be found in U.S. Patent Application Publication Number 2018/0064388, filed Feb. 21, 2017, and entitled "Methods and Systems for Labeling Sleep States," which is hereby incorporated herein, in its entirety, by reference. Another convention is to ascribe power in the HF band to parasympathetic activation, and power in the LF band to a mixture of sympathetic and parasympathetic activation. Other HRV parameters calculated can include:

ApEn, the approximate entropy of the PP series;

SDNN, the standard deviation of NN intervals, often calculated over a 24-hour period;

SDANN, the standard deviation of the average NN intervals calculated over short periods, usually 5 minutes (SDANN is therefore a measure of changes in heart rate due to cycles longer than 5 minutes, while SDNN reflects all the cyclic components responsible for variability in the period of recording, therefore it represents total variability);

RMSSD ("root mean square of successive differences"), the square root of the mean of the squares of the successive differences between adjacent NNs;

SDSD ("standard deviation of successive differences"), the standard deviation of the successive differences between adjacent NNs;

NN50, the number of pairs of successive NNs that differ by more than 50 ms; and pNN50, the proportion of NN50 divided by total number of NNs.

The independent estimates of cycle length from each of these variables can be combined into a common estimate by weighting of the variables.

In one embodiment, an overnight heart rate recording for a user can first be divided into various sleep stages, such as may include light sleep, deep sleep, and rapid eye movement ("REM") sleep. The HRV parameters and HR can then be calculated for a stage of sleep only, rather than for the entire night, if desired. A model of the RHR (or a metric derived from HRV) calculated only over the non-REM sections of sleep (e.g., light sleep and deep sleep) can be used in connection with predictive models for purposes discussed herein.

In another embodiment, a person's breathing rate can be extracted from the PPG signal. The breathing rate would typically be measured to be between twelve and twenty breaths per minute. An average breathing rate can be extracted for each night or a set of nights. The subject's activity level can also be tracked, which can be used to correct confounders such as heavy exercise and other intense physical activity which may affect the resting HR and HRV parameters used in the predictive models.

Concurrently with the analysis and predictions in at least some embodiments, HR information such as the RHR can be monitored for the user. As mentioned, this may include using the monitoring device 102 during a sleep period and after a minimum period of inactivity to obtain RHR date for the user using one or more approaches as discussed and suggested herein. If it is determined that there is no resting heart rate pattern information available, then the process can continue without utilizing such pattern information.

Again, these HR data and other metrics can be used to predict mental health issues, and in some embodiments combinations of these metrics and approaches can be used to attempt to improve the accuracy of the predictions. In other embodiments, two or more measurements can be combined to attempt to improve the predictions, whether using user input-based predictions as discussed above or based upon measured or detected body and health data alone. For example, in one embodiment a user's HR information and blood or tissue chemistry can be used to screen for mental state. For example, there may be variations in the concentration or number of red or white blood cells, or the concentration or amount of hemoglobin, ferritin, serum iron, peripheral capillary oxygen saturation ($SpO_2$), water, lipid, collagen, sebum, or other components typically found in a person's blood or skin tissue or the surface of the skin. Variations in body temperature can also be determined using a temperature sensor.

A monitoring device 102 in accordance with various illustrative embodiments can perform non-invasive real-time measurement of hemoglobin and water content (e.g., a hemoglobin to water ratio, or relative changes in just hemoglobin or water concentration in the blood and tissue) in a user's body using optical emitters, sensors, and other components such as those discussed and suggested herein. The amount of light absorption in human skin can vary with differences in hemoglobin and water concentration. This can be particularly noticeable for light having wavelengths in the infrared ("IR") or near-IR spectrums. As the hemoglobin concentration decreases, the amount of light absorption due to hemoglobin decreases. The amount of light absorption will also change by a different amount based on changes in oxygen saturation, and the absorption differences are more pronounced at different wavelengths. Accordingly, in some embodiments a monitoring device 102 might include a first emitter at a first wavelength and second emitter at a second wavelength appropriate for detecting variations in hemoglobin and water concentration, while in other embodiments the device 102 might include a third emitter at a second wavelength appropriate for detecting variations in $SpO_2$, while some tracking devices 102 can include both (or an emitter assembly capable of selectively or concurrently emitting light in both target wavelength bands. In one embodiment, a monitoring device 102 can include two light-emitting diodes (LEDs) with two wavelengths in the range of about 600-1000 nm to detect changes in $SpO_2$ and hemoglobin content, and another LED with a wavelength in the range of 1000-1500 nm for measuring variations in water content, and for measuring hemoglobin to water ratios when combined with one of the first two LEDs.

As with resting heart rate data illustrated in FIGS. 2A and 2B, values for metrics such as hemoglobin, water concentration, and $SpO_2$ can be cyclical. By monitoring how these metrics vary in the user's body over time, and how these variations correspond to mental state, measurements of the metrics can be used to predict timing of mental health-related events and episodes. Changes in these parameters also can be indicative or other potential issues in a user's body, and thus can be used in some embodiments to recommend seeing a physician or taking other action.

In some embodiments a software application might ask questions of a user in response to detected changes to the user's body. For example, changes in sleep pattern might be due to changes in location or stress. Other changes, such as new medicines or exercise patterns, might influence at least some of the measurements as well. By obtaining this information, the software can determine whether to exclude certain values or periods of time, whether to weight those values differently, etc. Information available from motion sensors or other activity tracking can also be used to attempt to determine some of these factors as well within the scope of the various embodiments.

With regard to hemoglobin concentration, in one embodiment, the concentration in a user's body is measured using an optical technique such as near-infrared ("NIR") spectroscopy. NIR approaches can utilize an emitter that emits radiation in the NIR spectrum, such as may have a wavelength in the range of 780 nm to 2500 nm. NIR has an advantage over other optical techniques in that it can penetrate the skin further than other optical techniques. Portions of the radiation that are not absorbed can be reflected back to one or more detectors having sensors able to detect radiation over at least the corresponding wavelength band. The absorption data determined by the detector(s) can be analyzed using a multivariate approach, such as principal component analysis ("PCA") or neural networks, among other such options, to determine information about the composition of the blood in the subject's body. One or more optically dispersive elements may be used to separate out specific wavelengths for measurement. In one example, two detectors are used at different positions in order to attempt to account for artifacts in the surface of the skin, as well as variations in the skin that might result from compression or other outside influences. The specific wavelength(s) used to measure hemoglobin and water concentration (e.g., between 900 and 1500 nm) can depend in part upon the specific implementation and design, as there can be a tradeoff between depth of penetration and sensitivity to variations in concentration, as some devices will have less sensitive detectors and some devices will be tight against the skin while some may have an amount of separation. Detectors of different materials, and thus different sensitivities and accuracies, can be used as well, as may include detectors made of silicon and indium gallium arsenide, among other such options. Devices in accordance with various embodiments may also utilize more than one emitter, having different wavelengths of emission, or emitters that emit more than one wavelength, etc. In some embodiments, the accuracy can depend in part upon the orientation of the device relative to the skin, the proximity to the skin, or any compression of the skin due to the device (such as by a tracker being worn tightly around the skin or being compressed by another portion of the body during sleep). Accordingly, in some embodiments a pressure sensor, camera, or other sensor can be used to attempt to account for such factors or variations.

Figure 3:
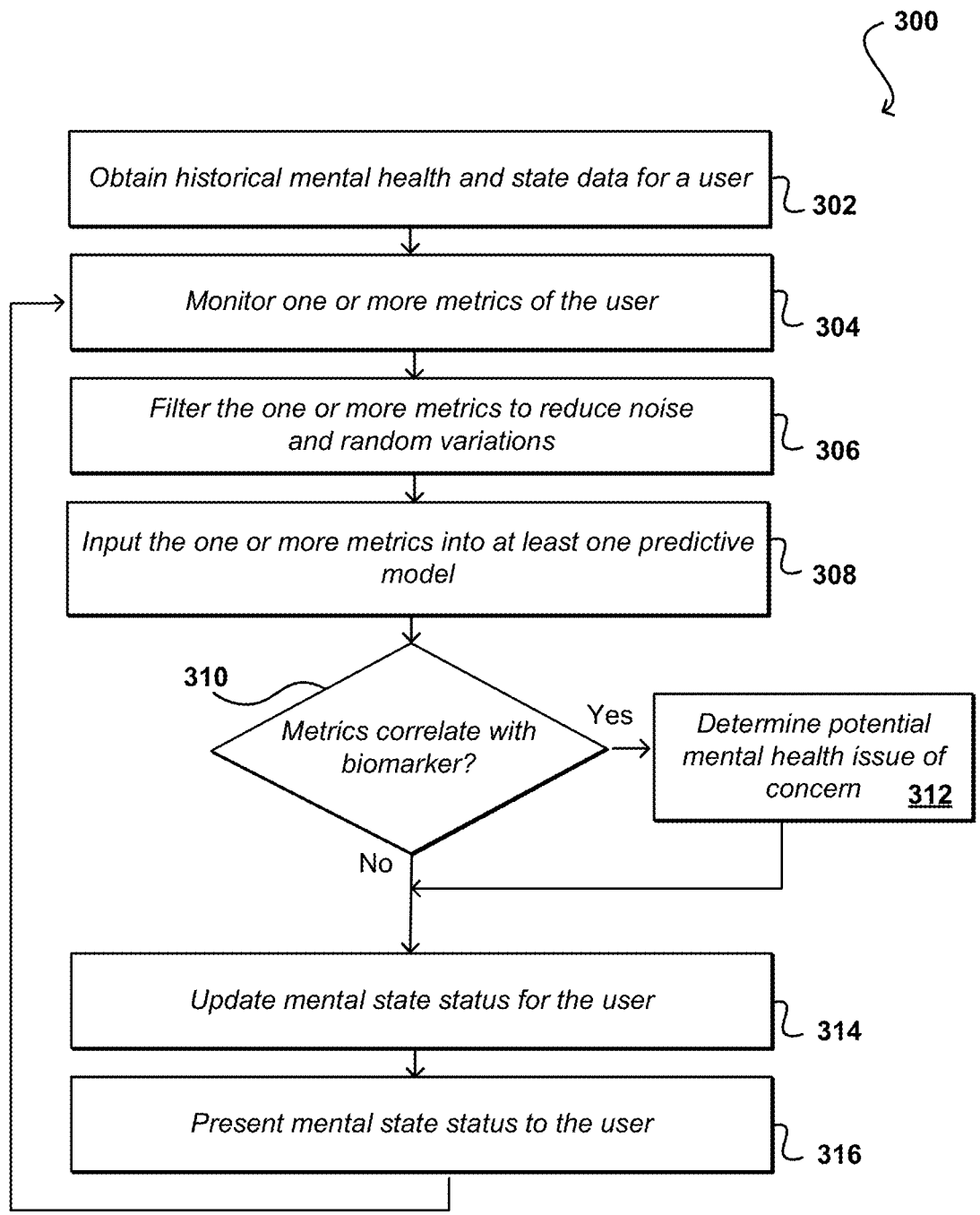
FIG. 3 illustrates an example process for determining and predicting mental state status in accordance with various embodiments.

FIG. 3 illustrates an example process 300 for determining the status of a user's mental state using information acquired in accordance with various embodiments. It should be understood that, for this and all other processes discussed herein, there can be additional, alternative, or fewer steps performed in similar or alternative orders, or in parallel, within the scope of the various embodiments unless otherwise stated. In this example, historical mental health and state information is obtained 302 for a user. This can include receiving manual input from the user or obtaining the data from another source, such as from an account or repository associated with a health monitoring device, among other such options. In some embodiments an application might provide an electronic diary or journal where the user can keep track of potentially-relevant information. While historical information may be available for use, the process does not require such information and can make determinations and predictions automatically, without requiring user input, based at least in part upon health information obtained or monitored for the user over time.

In this exemplary method, physiological data and related metrics for a current mental state of a user can be procured and monitored 304 over time. These can include any physiological data, including, but not limited to, that discussed or suggested herein, such as HR, RHR, $SpO_2$, hemoglobin concentration, water retention, skin sebum or collagen content, lipid content in blood or interstitial tissue, sleep logging, sleep quality, sleep duration, sleep stages architecture (including, but not limited to, time from sleep onset, total time in bed, total awake time), HRV metrics during the day and during sleep, HR-derived metrics, time spent in different HR zones, breathing rate, active minutes, exercise logging, altimeter changes, step count, food logs, water logs, weight measurements, body mass index, body impedance analysis, mood logs, symptom logging, changes in time zones, location, body basal temperature, oral temperature, in-ear temperature, hormonal levels as detected by urine or blood test samples, and the like. In one example, data for RHR and hemoglobin concentrations can be collected using a selection of optical sensors as discussed herein, although other approaches can be used as well. It should be understood that the data discussed herein are merely by way of example and that other combinations or types of metrics and information can be used as well within the scope of the various embodiments.

The physiological data can be collected over time, then filtered 306 to reduce noise and random variations in the data, which may be due to natural variations as well as outside influences such as changes in exercise, diet, stress, and sleep. Other types of processing of the data can be used as well as would be apparent to one of ordinary skill in the art in light of the teachings and suggestions contained herein. As mentioned, in various embodiments, measurements can be made during periods of rest or sleep, where there will be relatively few changes in position over a period of time. Changes in oxygen or hemoglobin signals can be triggered by movements or changes in position, such that periods of rest may provide more accurate or consistent results, or representations of the true state of the body independent of many external factors. In some embodiments, a monitoring or other associated device can utilize accelerometers, altimeters, inertial sensors, or other such components to monitor movement, and the device might wait until the subject has been still (within an allowable threshold amount of movement) for at least a determined period of time of inactivity to take measurements. This can provide sufficient time for the levels to reach an equilibrium point, thereby allowing for greater accuracy in at least some embodiments.

The filtered data collected over time can be analyzed to determine or update patterns determined for the respective metrics. This step can include inputting 308 the physiological data into one or more predictive models to identify 310 whether the physiological data, including any pattern found therein, correlates with one or more biomarkers relevant to mental state. Biomarkers used for comparison with the physiological data are open-ended and include, but are not limited to, the following:

Low levels of activity (mean total minutes per day with heart rate in cardio or peak zones; when this biomarker has a lower value, depression risk is higher, for example);

Variable sleep (standard deviation of minutes asleep per night or standard deviation of bedtime or wake-up time; when this biomarker has a higher value, depression risk is higher);

High resting heart rate (maximum (or mean) resting heart rate; when this biomarker has a higher value, depression risk is higher);

Rapid sleep onset latency (mean minutes between bedtime and onset of sleep; when this biomarker has a higher value, depression risk is lower);

Low mean steps per day (when this biomarker has a higher value, depression risk is higher);

Long periods or gaps of wakefulness during a sleep period (i.e., highly-disrupted sleep; when this biomarker has a higher value, depression risk is higher);

Low heart rate variability (when this biomarker has a higher value, depression risk is higher);

Late bedtimes (when this biomarker has a higher value, depression risk is higher); and Slow REM onset latency (when this biomarker has a higher value, depression risk is higher).

The predictive models can update pattern information based on additional data to obtain more accurate pattern information. In some embodiments, the state data may be weighted or decayed such that recent physiological data has more of an impact on pattern determination to account for changes in the health of the user, such as changes in age, hormone levels, and the like. While current information can be sufficient to form a screening or initial analysis, the predictive models will become more accurate as additional information is received and analyzed.

Various algorithms and approaches can be used to analyze and correlate the physiological data within the scope of the various embodiments. Information about the user's body can be obtained by a monitoring device 102 or other such tracking device that can be correlated with mental state and health information. This can include information known across various individuals as a base pattern, but also can be updated or determined for a specific person to provide more accurate predictions. The analyses, correlations, and determinations can be done by advanced signal processing methods, averaging, or otherwise aggregating data obtained over additional time periods and/or by feeding the data into a machine learning algorithm, among other such options. The physiological data can be used to generate predictions based on any determined patterns. Further, as changes in the RHR information are determined over time, for example, predictions can be updated, such as when RHR becomes indicative of a beginning of a depressed or anxious state.

The data can be provided as inputs to a predictive modeling or machine learning process that can use the information to predict future mental states. As mentioned, there may be various physiological data inputs, as may relate to heart rate, activity, sleep, and others discussed herein. Patterns can be determined and used for each available type of data to attempt to come to a more accurate determination. The data values may be weighted by different amounts, such as may be based upon strength of prediction or accuracy, among other such factors. These weightings can be updated or modified over time, such as may be based upon machine learning or changes in a user's body or state, etc. There may also be different confidence levels or other factors that can impact the relative weightings as well. The weight values chosen can also depend on the signal-to-noise ratio of some signals.

As discussed, there might be one pattern generated in some embodiments that is a function of both RHR and sleep data, or other such metrics. In some embodiments a deep neural network or other machine learning approach can be used to "learn" pattern based on the obtained metrics, among other such information. Various other predictive modeling patterns and approaches can be used as well, including those discussed and suggested herein. Correlations and patterns, discerned through the predictive modeling, can be used to predict a timing of a next occurrence of a mental health-related event, as well as potentially other related events as well. The pattern and correlation information may be updated in some embodiments any time additional information is provided or obtained.

As mentioned, the predictive modeling can use and apply various types of information which may impact data values for differing bodies. For example, information may be obtained about the amount of exercise or physical activity a person has undergone during a given day or period, which may account for differences in detected physiological data values as discussed herein. There may also be variations in diet, stress, weight, body fat percentage, body mass index ("BMI"), medication, or other such factors that can be accounted for as well. In at least some embodiments, these and other such factors can be fed into one or more predictive modeling schema and then a regression applied in order to verify conditions for accurate predictions. Should a correlation with one or more biomarkers be found, at least a potential mental health issue may be determined 312 for the user. The process can continue and repeat, updating 314 the mental state status for the user, and additional types of information can be added into the process for consideration as the information becomes available. In at least some embodiments, the recommendations or weightings may change over time, such as for changes in the body or exercise levels, age, and the like.

Once the mental state status is generated or updated, that can be outputted or exposed 316 to the user or another appropriate or authorized entity. The mental state status information can be surfaced in a number of different ways. There can be various options through which a user can navigate, or there can be specific interfaces or displays provided, among other possibilities. In some embodiments, the symptoms of various users can be determined and the application can predict when those users will suffer from mental health-related maladies, with corresponding notifications delivered to the users. A given application might also provide different views depending upon a user's goals. In some embodiments, the app might also provide recommendations for improving health or achieving the goal, based at least in part upon the monitored health information. Recommendations can also be made to see a doctor in cases where the physiological and other data might indicate a potential medical condition.

As mentioned, the various embodiments can be implemented as a system that includes one or more monitoring/tracking devices for a given user. In other embodiments the embodiments may be provided as a service, which users can utilize for their devices. Other fitness tracker and health care providers may also subscribe or utilize such a service for their customers. In some embodiments, an application programming interface ("API") or other such interface may be exposed that enables collected physiological data, and other information, to be received by the service, which can process the information and send the results back to the monitoring or related computing device, for access by the user. In some embodiments at least some of the processing may be done on the monitoring or tracking device itself, but processing by a remote system or service may allow for more robust processing, particularly for tracking devices with limited capacity or processing capability.

Figure 4:
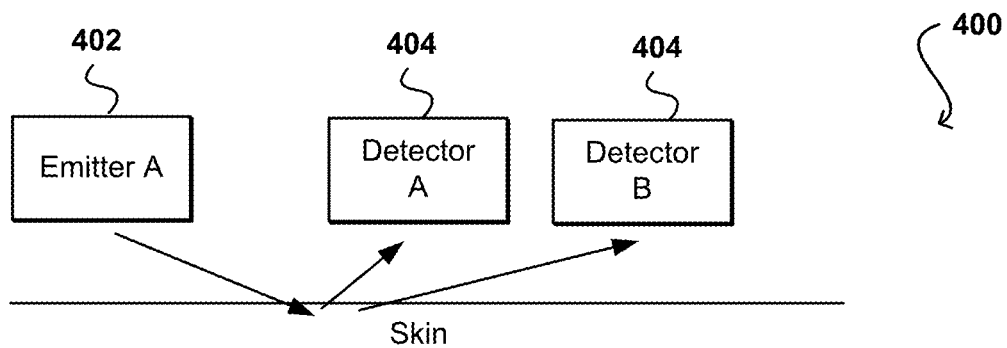
FIG. 4 illustrates example monitoring device light paths that can be utilized in accordance with various embodiments.

As may be seen in the illustrative embodiment 400 depicted with the aid of FIG. 4, light emitted from one or more emitters 402 can be reflected from the skin back to the detectors 404. Although a user in various embodiments may wear a monitoring device, such as a smartwatch or fitness tracker, or another PPG device proximate to a wrist location, in other embodiments such a device may be worn in locations such as the ear, fingertips, ankle, neck, upper arm, torso, leg and/or forehead (e.g., such that light sources of the PPG devices are adjacent to blood vessels of a human). Two detectors 404 are used at differing positions in this embodiment, to account for artifacts in the surface of the skin, as well as variations in the skin that might result from compression or other outside influences.

The path light travels from an emitter 402 to the skin and back to one of the detectors 404 can be referred to as a "light path." In addition to having its ordinary meaning, a light path can refer to the probabilistic path of photons from one location to another, typically from the light source (or emitter) to the light sensor (or detector). Photons released by the emitter 402 will follow many different paths to each detector 404. For simplicity and clarity, the path that results from the optical power-weighted average of all the possible paths is described simply as the light path in some embodiments. In some alternative embodiments, "light path" refers to the path along which most of the photons travel. In yet other embodiments, "light path" refers to an approximated vector having an origin at a center of a light source and terminating anywhere in the surface area of a detector 404, and representing an approximate path of light from the emitting source 402 to the detector 404.

As a light path represents an approximate path of light from a given emitter source 402 to a given detector 404, for example, if there are multiple emitters 402 and multiple detectors 404, then a distinct light path exists between each of the multiple sources and each of the multiple detectors. Consistent with the embodiments described herein, PPG signals associated with any of the aforementioned light paths may be selectively obtained and utilized for estimating HR and/or other physiological metrics. For example, the PPG signals corresponding to any of multiple paths may be compared using a quality/confidence metric such as a signal-to-noise ratio ("SNR"), and the PPG signal having the highest quality can be selected to be used for estimating the HR and/or other physiological data.

Figure 5:
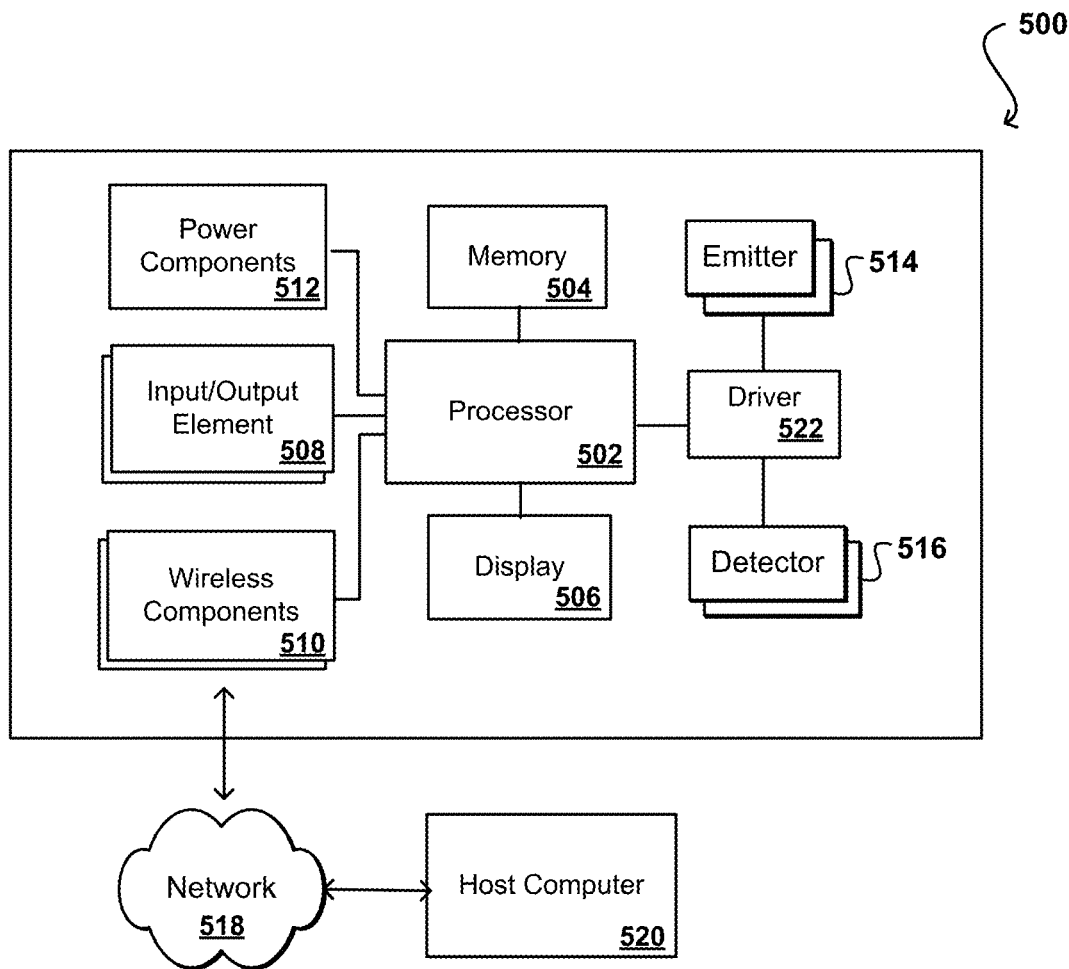
FIG. 5 illustrates components of an example network-connected monitoring device that can be utilized in accordance with various embodiments.

FIG. 5 illustrates components of an example mental state screening and prediction system 500 that can be utilized in accordance with various embodiments. In this example, a monitoring or tracking device includes at least one processor 502, such as a central processing unit ("CPU") or graphics processing unit ("GPU") for executing instructions that can be stored in a memory device 504, such as may include flash memory or DRAM, among other such options. As would be apparent to one of ordinary skill in the art, the device can include many types of memory, data storage, or computer-readable media, such as data storage for program instructions for execution by a processor. The same or separate storage can be used for images or data; a removable memory can be available for sharing information with other devices, and any number of communication approaches can be available for sharing with other devices. The device typically will include some type of display 506, such as a touch screen, organic light emitting diode ("OLED"), or liquid crystal display ("LCD"), although devices might convey information via other means, such as through audio speakers or projectors.

A monitoring device or similar tracking device will include at least one motion detection sensor, which, as illustrated, can include at least one I/O element 508. That type of sensor can determine and/or detect orientation and/or movement of the device. Such an element can include, for example, an accelerometer, inertial sensor, altimeter, or gyroscope operable to detect movement (e.g., rotational movement, angular displacement, tilt, position, orientation, or motion along a non-linear path) of the device. An orientation-determining element can also include an electronic or digital compass, which can indicate a direction (e.g., north or south) in which the device is determined to be pointing (e.g., with respect to a primary axis or other such aspect). A device may also include an I/O element 508 for determining a location of the device (or the user of the device). Such a positioning element can include or comprise a Global Positioning System ("GPS") or similar location-determining element(s) operable to determine relative coordinates for a position of the device. Positioning elements may include wireless access points, base stations, etc., that may either broadcast location information or enable triangulation of signals to determine the location of the device. Other positioning elements may include QR codes, barcodes, RFID tags, NFC tags, etc., that enable the device to detect and receive location information or identifiers allowing the device to obtain the location information (e.g., by mapping the identifiers to a corresponding location). Various embodiments can include one or more such elements in any appropriate combination. The I/O elements 508 may also include one or more biometric sensors, optical sensors, barometric sensors (e.g., altimeter), and the like.

As mentioned above, some embodiments use the element(s) to track the location and/or motion of a user. Upon determining an initial position of a device (e.g., using GPS), the device may track of the location of the device by using the element(s), or in some instances, by using the orientation determining element(s) as mentioned above, or a combination thereof. As should be understood, the algorithms or mechanisms used for determining a position and/or orientation can depend at least in part upon the selection of elements available to the device. The example device also includes one or more wireless components 510 operable to communicate with one or more electronic devices within a communication range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections as known in the art. The device also includes one or more power components 512, such as may include a battery operable for recharging through conventional plug-in approaches or through other approaches such as capacitive charging through proximity with a power mat or other such device. In some embodiments, the device can include at least one additional input/output device 508 able to receive conventional input from a user. This conventional input can include, for example, a push button, touch pad, touch screen, wheel, joystick, keyboard, mouse, keypad, or any other such device or element whereby a user can input a command to the device. These I/O devices 508 could even be connected by a wireless infrared or Bluetooth or other link as well in some embodiments. Some devices also can include a microphone or other audio capture element that accepts voice or other audio commands. For example, a device might not include any buttons at all, but might be controlled only through a combination of visual and audio commands, such that a user can control the device without having to be in contact with the device.

As mentioned, many embodiments will include at least some combination of one or more emitters 514 and one or more detectors 516 for measuring data for one or more metrics of a human body, such as for a person wearing the tracker device. In some embodiments, this may involve at least one imaging element, such as one or more cameras that are able to capture images of the surrounding environment and that are able to image a user, people, or objects in the vicinity of the device. The image capture element can include any appropriate technology, such as a CCD image capture element having a sufficient resolution, focal range, and viewable area to capture an image of the user when the user is operating the device. Methods for capturing images using a camera element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application, or other device.

In line with the optical-oriented discussions herein, the example device in the FIG. 5 system includes emitters 514 and detectors 516 capable of being used for obtaining optical photoplethysmogram ("PPG") measurements. Some PPG technologies rely on detecting light at a single spatial location, or adding signals taken from two or more spatial locations. Both of these approaches result in a single spatial measurement from which the HR estimate (or other physiological data) can be determined. In some embodiments, a PPG device employs a single light source 514 coupled to a single detector 516 (i.e., a single light path). Alternatively, a PPG device may employ multiple light sources 514 coupled to a single detector or multiple detectors 516 (i.e., two or more light paths). In other embodiments, a PPG device employs multiple detectors 516 coupled to a single light source or multiple light sources 514 (i.e., two or more light paths). In some cases, the light source(s) 514 may be configured to emit one or more of green, red, and/or infrared light. For example, a PPG device may employ a single light source 514 and two or more light detectors 516 each configured to detect a specific wavelength or wavelength range. In some cases, each detector 516 is configured to detect a different wavelength or wavelength range from one another. In other cases, two or more detectors 516 are configured to detect the same wavelength or wavelength range. In yet another case, one or more detectors 516 are configured to detect a specific wavelength or wavelength range different from one or more other detectors). In embodiments employing multiple light paths, the PPG device may determine an average of the signals resulting from the multiple light paths before determining an HR estimate or other physiological metrics. Such a PPG device may not be able to resolve individual light paths or separately utilize the individual signals resulting from the multiple light paths.

In some embodiments a user wearing a monitoring device with PPG functionality might perform an activity involving motion (or contorting of the wrist, for example, for a wrist-worn PPG device, thereby affecting the dynamics of the blood flow within the wrist). In such instances the accuracy of the HR estimate provided by the PPG device may be reduced or compromised. The light intensity received by the light detectors 516 may be modulated by these movements typically at an order of magnitude or greater than the desired cardiac signal. Therefore, a preprocessing step where the signal effect of these movements is removed can be utilized to improve HR estimation accuracy during motion. In addition to the deleterious effects of motion, another cause of reduced signal quality in PPG devices may be the characteristics of the local area being sensed. For instance, signal quality can vary dramatically if a wrist-worn PPG sensor is moved only a few millimeters up or down the wrist. In addition, during motion, certain portions of the wrist-worn PPG devices may be subject to more motion depending on their location, position, and/or orientation, and PPG sensors placed on such portions may therefore result in greater degradation of the PPG signal due to motion.

Various embodiments enable a PPG device to utilize signals based on two or more independently addressable source-detector combinations such that the signal quality of the PPG device is improved, especially during activities involving motion. In some embodiments, PPG signals can be acquired via multiple light paths involving one or more sources and one or more detectors placed at different spatial locations. These multiple PPG signals can then be processed to isolate the cardiac component (e.g., by removing the motion component) from the PPG signals. For example, the motion component may be removed based on inputs from the accelerometer, unsupervised learning and/or previously done supervised learning. Additionally, or alternatively, the PPG signals corresponding to these multiple light paths are compared using a quality metric such that the highest-quality PPG signal can be selected for estimating HR or other physiological metrics, as well as sleep time or other potential aspects.

In order to utilize two or more source-detector pairs for motion signal rejection, a PPG device in accordance with various embodiments can use a computer program to identify the motion component of a given signal and remove the motion component from the composite signal, leaving only the cardiac signal as a remainder. In some implementations, the temporal phase of the cardiac waveform is assumed to stay constant between different light paths, while the phase of the motion signal is expected to vary between light paths, due to how the PPG sensor interacts with the skin surface during activities involving motion (e.g., pressure at the PPG/skin interface may vary depending on the spatial location of the light source and the light detector of the light path). Using this concept, PPG devices can fit mathematical models to the spatial light path signals to identify the cardiac and motion components. First, PPG signals are extracted by each source-detector combination. For example, two light sources 514 and two light detectors 516 would result in four source-detector combinations. A mathematical model can then be fit to the different spatial points, from which characteristic signals are extracted related to the cardiac and motion components of the PPG signals. PPG devices may also implement other techniques including, but not limited to, independent component analysis ("ICA") and other forms of blind source separation.

Although some embodiments are described with reference to HR or cardiac components of PPG signals, the techniques described herein may be extended to other types of physiological data described herein, such as may relate to $SpO_2$ or other types of signals that can be extracted from the PPG signals to determine physiological data or metrics. For example, in some embodiments, a method for determining an $SpO_2$ value comprises receiving a first set of one or more PPG signals from one or more PPG sensors 516, which may include analog signals or digital data sampled from analog components and stored in computer memory. The first set of PPG signals may correspond to red and/or infrared light previously emitted by one or more emitters 514 after the emitted light has interacted with the user's skin, when the monitoring device is worn by the user. A first set of PPG signals may include a noise component. The method for determining the $SpO_2$ value may further comprise receiving a second set of one or more PPG signals from the one or more PPG sensors or detectors, which may include analog signals or digital data sampled from analog components and stored in computer memory. For example, the second set of PPG signals may be obtained from different ranges of wavelengths emitted from the light source 514 than the first set of PPG signals. The second set of PPG signals may be obtained from one or more green light sources 514. In some cases, the second set of PPG signals is obtained from a system within the device used for tracking a user's heart rate. In other cases, the second set of PPG signals is received from a system separate from HR detection. The method for determining the $SpO_2$ value may further comprise filtering the first set of PPG signals based on a feature of the second set of PPG signals, to generate a filtered set of PPG signals. Various filtering techniques may be used to remove noise or other features from the first set of PPG signals based on a feature of the second set of PPG signals. As but one example, HR may be the feature of the second set of PPG signals. In the case of HR, the device may create a filter based at least in part upon the detected frequency of the HR signal. Examples of filters include a low-pass filter, a high-pass filter, and a narrow-band filter that excludes frequencies that are inconsistent with the frequency of the HR signal. The method for determining the $SpO_2$ value may further comprise using one range of wavelengths to better measure an underlying signal on which the wavelengths of the first set of PPG signals operates. Based on this underlying signal (or features derived therefrom), the device can improve the first set of PPG signals based on filtering noise from the first set of PPG signals. Further, the filtered set of PPG signals can be used to create and store a $SpO_2$ value. As an example, the filtered set of PPG signals may have a reduced or eliminated noise component and therefore may serve as a more accurate basis for creating and storing the $SpO_2$ value.

In some embodiments, an intermediate HR estimation can be performed based on PPG signals from two or more light paths. For each of the acquired PPG signals, the PPG device may determine an estimate of the HR in beats-per-minute ("BPM") and compute a confidence metric associated with the PPG signal, indicative of the signal quality for the particular light path associated with the PPG signal. It may also be possible to compute a confidence metric without an intermediate HR estimation, for example via characteristics (e.g., statistics) of the PPG signal or filtered versions of the PPG signal. In some embodiments, each confidence metric corresponds to a single PPG signal. In other cases, each confidence metric corresponds to multiple PPG signals. By way of specific example, a confidence metric may be computed for each way of combining the PPG signals (e.g., signals A+B, signals A+C, signals B+C, and signals A+B+ C), as well as for various combinations of PPG signals (e.g., selecting at least two of signals A, B, and C). In other cases, one confidence metric corresponds to a single PPG signal and another confidence metric corresponds to a combination of multiple PPG signals. The PPG device can select an HR estimate from the multiple HR estimates corresponding to the multiple light paths (e.g., by selecting the HR estimate of the PPG signal having the highest confidence metric). Alternatively, the PPG device may assign different weight values to the multiple HR estimates based on the confidence metric values associated with the individual and/or multiple PPG signals and compute a final HR estimate based on the weight values. As with other aspects of the present disclosure, the confidence values and/or the weight values may be updated or optimized using machine learning. The PPG device may implement hysteresis logic which prevents jumping between light paths in a short time window if the confidence metric values corresponding to the two light paths are within a threshold value. The PPG device may also implement logic configured to bias the selection of HR estimates based on user data, activity data, movement data, or other data accessible by the PPG device. The PPG device may apply a smoothing filter on the HR estimates to, for example, improve accuracy and provide a better user experience.

One advantage of such an approach lies in the fact that the spatial information associated with the light sources 514 and/or light detectors 516 can be used by different algorithms to improve HR or other physiological metric estimation accuracy of the PPG sensing device, especially when the user of the device is exercising or performing activities involving motion. Existing implementations typically rely on algorithms to improve the HR or other physiological metric estimation performance, but do not have the benefit of the extra sensor data generated based on multiple light paths.

Referring to FIG. 5, an example PPG monitoring device may comprise one or more processors 502 coupled to memory 504, a display 506, a bus, one or more input/output (I/O) elements 508, and wireless networking components 510, among other such options. A display 506 and/or I/O devices 508 may be omitted in certain embodiments. If included, a display 506 may provide an interface for displaying data, such as HR, blood oxygen saturation (SpO$_2$) levels, and other metrics of the user. For example, the processor 502 may compute values for the physiological metrics monitored by the PPG device based on one or more PPG signals generated by detectors 516 of light. In an embodiment, the PPG device is a wristband, and the display is configured such that the display 506 faces away from the outside of a user's wrist when the user wears the PPG device. In other embodiments, the display 506 may be omitted and data detected by the PPG device may be transmitted using the wireless networking interface via near-field communication ("NFC"), Bluetooth, Wi-Fi, or other suitable wireless communication protocols over at least one network 518 to a host computer 520 for analysis, display, reporting, or other such use.

The memory 504 may comprise RAM, ROM, FLASH memory, or other non-transitory digital data storage, and may include a control program comprising sequences of instructions which, when loaded from the memory and executed using the processor 502, cause the processor 502 to perform functions described herein. The emitters 514 and detectors 516 may be coupled to a bus directly or indirectly using driver circuitry 522 by which the processor 502 may drive the light emitters 514 and obtain signals from the light detectors 516. The host computer 520 may communicate with the wireless networking components 510 via one or more networks 518, which may include one or more local area networks, wide area networks, and/or the internet using any of terrestrial or satellite links. In some embodiments, the host computer 520 executes control programs and/or application programs configured to perform some of the functions described herein.

In some embodiments, each emitter 514 can be individually controlled, or each light detector 516 can be individually read out when multiple detectors 516 are used, and in such embodiments, PPG sensor data along several different light paths can be collected. The control program can utilize the collected data to provide a more accurate estimation or HR and/or other physiological metrics. In related aspects, the processor 502 and other component(s) of the PPG monitoring device may be implemented as a System-on-Chip ("SoC") that may include one or more CPU cores that use one or more reduced instruction set computing ("RISC") instruction sets, and/or other software and hardware to support the monitoring device.

In various embodiments, the emitters (or light sources) 514 comprise electronic semiconductor light sources, such as LEDs, or produce light using any of filaments, phosphors, or laser. In some implementations, each of the light sources 514 emits light having the same center wavelength or within the same wavelength range. In other cases, at least one light source 514 may emit light having a center wavelength that is different from another one of the light sources 514. The center wavelengths of the light emitted by the light sources 514 may be in the range of 495 nm to 570 nm. For example, a particular green light source 514 may emit light with a center wavelength of 528 nm. In other embodiments, one or more of the light sources 514 may emit red light (e.g., 660 nm center wavelength) or IR light (e.g., 940 nm center wavelength). In some embodiments, one or more of the light sources 514 may emit light with peak wavelengths typically in the range of 650 nm to 940 nm. More particularly, a red light source 514 may emit light with a peak wavelength of 660 nm, and one or more infrared light sources 514 may emit light with peak wavelengths in the range of 750 nm to 1700 nm. By way of example and not any sort of limitation, a particular infrared light source 514 may emit light with a peak wavelength of 730 nm, 760 nm, 850 nm, 870 nm, or 940 nm. In some cases, commercial light sources such as LEDs may provide output at about 20 nm intervals with a center wavelength tolerance of +/−10 nm from the manufacturer's specified wavelength and thus one possible range of useful peak wavelengths for the light sources is 650 nm to 950 nm. The green light sources 514 may be configured to emit light with wavelengths in the range of 495 nm to 570 nm. For example, a particular green light source 514 may emit light with a wavelength of 528 nm. The green light sources 514 may be as equally spaced from light detectors 516 as the pairs of red and infrared light sources 514. If, say, the distance between light detectors 516 and a center of a first red light source 514 is 2 mm, the distance between light detectors 516 and a green light source 514 may also be 2 mm (e.g., equidistant). In some other cases, the distance between the light detectors 516 and one or more light sources 514 is not equidistant. Further, in some embodiments, one or more of the light sources 514 may comprise a single LED package that emits multiple wavelengths, such as green, red and infrared wavelengths, at the same or substantially the same (e.g., less than 1 mm difference) location with respect to multiple detectors 516. Such LEDs may include multiple semiconductor elements co-located using a single die in a single package.

The spacing of the light sources 514 may be measured from the side of the light source 514 or the center of the light source 514. For example, the light sources 514 may be configured such that the center of each light source 514 is at a first distance from the edge of the closest one of the light detectors 516. In an illustrative embodiment, the first distance may be 2 mm. In some implementations, each light source 514 is located at a second distance from the closest one of the light sources 514, and each light detector 516 is located at a third distance from the closest one of the light detectors 516. In some embodiments, the second and third distances are identical to the first distance. In other embodiments, each of the second and third distances is different from the first distance. The second distance may be identical to or different from the third distance. The particular magnitude of the spacing may depend on a number of factors and this disclosure does not limit the embodiments to any particular spacing. For example, spacing in a range of 1 mm (or less) to 10 mm would be workable in various embodiments.

In some embodiments, independent control of all light sources 514 is provided. In other embodiments, several light sources 514 are controlled together as a gang or bank. A benefit of independent control of each light source 514, or independent readout from each of multiple detectors 516 (e.g., obtaining independent signals based on the same or different light wavelengths from each of multiple detectors), is that a multiple light path approach may be used to improve the estimation of HR and/or other physiological metrics, as discussed herein.

Light detectors 516 may comprise one or more sensors that are adapted to detect wavelengths of light emitted from the light sources 514. A particular light source 514 combined with a particular detector may comprise a sensor such as a PPG sensor. A first PPG sensor and a second PPG sensor can share components, such as the same light sources 514 and/or detectors 516, or have different components and thus the term "PPG sensor," in addition to having its ordinary meaning, may refer to any of such arrangements although actual embodiments may use multiple components in implementing a PPG sensor. The term "PPG device," in addition to having its ordinary meaning, may refer to any device including a PPG sensor. A light detector 516, in an embodiment, may comprise one or more detectors 516 for detecting each different wavelength of light that is used by the light sources 514. For example, a first detector 516 may be configured to detect light with a wavelength of 560 nm, a second detector 516 may be configured to detect light with a wavelength of 940 nm, and a third detector 516 may be configured to detect light with a wavelength of 528 nm. Examples include photodiodes fabricated from semiconductor materials and having optical filters that admit only light of a particular wavelength or range of wavelengths. The light detectors 516 may comprise any of a photodiode, phototransistor, charge-coupled device ("CCD"), thermopile detector, microbolometer, or complementary metal-oxide-semiconductor ("CMOS") sensor. The light detectors 516 may comprise multiple detector elements, as further described herein. One or more of the detectors 516 may comprise a bandpass filter circuit.

In other embodiments, a detector 516 may comprise one or more detectors 516 configured to detect multiple wavelengths of light. For example, a single detector 516 may be configured to tune to different frequencies based on data received from an electrical digital microprocessor coupled to detectors. In another way, the single detector 516 may include multiple active areas where each active area is sensitive to a given range of wavelengths. A single detector 516 may be configured to detect light with wavelengths in the red and IR frequencies, and a second detector 516 is configured to detect light with wavelengths in the green frequencies. Further, each of the light sources 514 may use any of one or more different wavelengths of light as previously described.

In an embodiment, light detectors 516 can be mounted in a housing with one or more filters that are configured to filter out wavelengths of light other than wavelengths emitted by light sources 514. For example, a portion of the housing may be covered with a filter which removes ambient light other than light in wavelengths emitted by light sources 514. Signals from light sources 514 may be received at the light detectors 516 through an ambient light filter that filters out an ambient light source generating ambient light with a wavelength differing from the wavelength that is detected by the detector 516. Although LEDs and photodiodes are used as examples of the light sources 514 and the light detectors 516, respectively, the techniques described herein may be extended to other types of light sources, such as edge emitting lasers, surface emitting lasers, and LED-pumped phosphors that generate broadband light. And the techniques may be extended to other combinations of light sources and detectors as well. For example, the PPG device may include: (i) single or multiple LEDs and a multi-element photodetector (e.g., a camera sensor); (ii) an LED array and single or multiple photodiodes; (iii) a broadband LED-pumped phosphor and detector array with wavelength selective filters on each detector; (iv) a spatial light modulator ("SLM") (e.g., a digital micromirror device ("DMD"); or (v) a liquid crystal on silicon ("LCoS") device) and single or multiple LEDs, other combinations thereof, or other configurations of light sources and detectors).

While certain flow discussions and diagrams are presented herein to illustrate various methods that may be performed by example embodiments, such merely illustrates example algorithms that may be programmed, using any suitable programming environment or language, to create machine code capable of execution by a CPU or microcontroller of the PPG device. In other words, the flow diagrams, together with the written description in this document, are disclosures of algorithms for aspects of the claimed subject matter, presented at the same level of detail that is normally used for communication of this subject matter among skilled persons in the art to which the disclosure pertains. Various embodiments may be coded using assembly, C, Objective-C, C++, Java, or other human-readable languages and then compiled, assembled, or otherwise transformed into machine code which can be loaded into ROM, EPROM, or other recordable memory of the monitoring device apparatus that is coupled to the CPU or microcontroller and then then executed by the CPU or microcontroller.

In an embodiment, PPG signals obtained from multiple light paths may be processed to filter or reject signal components associated with motion of the user, using a computer application or program to identify the motion component of the signal and remove the identified motion component from the composite signal, leaving the cardiac component as a remainder or final signal. PPG signals might be collected in variety of activities during day or at night, such as may relate to periods of walking, exercise, or sleep. Other on-device sensors including an accelerometer, gyroscope, or altimeter may be used to categorize or detect the activity, or human posture as a basis to develop the appropriate filters. These filters or signal processing methods might be used for targeted reduction of variability in the PPG data with multiple light paths. As an example and not a limitation, the accelerometer data can be used to develop signal processing methods to filter the PPG data and look into a certain posture, removing other body orientations.

This can help reduce the noise in the PPG data and get a better assessment of the corresponding physiological variables for the corresponding light paths.

In various embodiments, approaches discussed herein may be performed by one or more of: firmware operating on a monitoring device or a secondary device, such as a mobile device paired to the monitoring device, a server, host computer, and the like. For example, the monitoring device may execute operations relating to generating signals that are uploaded or otherwise communicated to a server that performs operations for removing the motion components and creating a final estimate value for HR, SpO$_2$, and/or other physiological data metrics. Alternatively, the monitoring device may execute operations pertinent to generating the monitoring signals and removing the motion components to produce a final estimate value for HR, SpO$_2$, and/or other physiological metrics local to the monitoring device. In this case, the final estimate may be uploaded or otherwise communicated to a server such as a host computer that performs other operations using the value.

An example monitoring or tracker device, such as one having components depicted in FIG. 5, can collect one or more types of physiological and/or environmental data from one or more sensor(s) and/or external devices and communicate or relay such information to other devices (e.g., a host computer or another server), thus permitting the collected data to be viewed, for example, using a Web browser or network-based application. For example, while being worn by the user, a monitoring device may perform biometric tracking via calculating and storing the user's step count using one or more sensor(s). The monitoring device may transmit data representative of the user's step count to an account on a Web service (e.g., www.fitbit.com), computer, mobile phone, and/or health station where the data may be stored, processed, and/or visualized by the user. As noted, the monitoring device may measure or calculate many other physiological data metrics in addition to, or in place of, the user's step count. Again, such physiological data may include, but are not limited to: energy expenditure (e.g., calories burned); floors climbed and/or descended; HR; heartbeat waveform; HR variability; HR recovery; respiration; SpO$_2$; blood volume; blood glucose; skin moisture; skin pigmentation level; location and/or heading (e.g., via a GPS, global navigation satellite system (GLONASS), or a similar system); elevation; ambulatory speed and/or distance traveled; swimming lap count; swimming stroke type and count detected; bicycle distance and/or speed; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality, and/or duration); pH levels; hydration levels; respiration rate; and/or other metrics.

An exemplary device for monitoring or tracking may also measure or calculate metrics related to the environment around the user (e.g., with one or more environmental sensor(s)), such as, for example, barometric pressure, weather conditions (e.g., temperature, humidity, pollen count, air quality, rain/snow conditions, wind speed), light exposure (e.g., ambient light, ultra-violet (UV) light exposure, time, and/or duration spent in darkness), noise exposure, radiation exposure, and/or magnetic field. Furthermore, a monitoring device (and/or the host computer and/or another server) may collect data from one or more sensors of the device and may calculate metrics derived from such data. For example, a monitoring device may calculate the user's stress or relaxation levels based on a combination of HR variability, skin conduction, noise pollution, and/or sleep quality. In yet another example, a monitoring device may determine the efficacy of a medical intervention, such as based on a combination of data relating to medication intake, sleep, and/or activity. Again, examples herein are provided for illustration only and are not intended to be limiting or exhaustive.

An example monitoring device may also include a computer-readable storage media reader, a communications device (e.g., a modem, a network card (wireless or wired), and/or an infrared communication device), and working memory 504 as described above. The computer-readable storage media reader can be connected with, or configured to receive, a computer-readable storage medium representing remote, local, fixed and/or removable storage devices as well as storage media for temporarily and/or more permanently containing, storing, transmitting, and retrieving computer-readable information. A monitoring system and various devices also typically will include a number of software applications, modules, services, or other elements located within at least one working memory device 504, including an operating system and application programs such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices, such as network input/output devices, may be employed.

Storage media and other non-transitory computer readable media for containing code, or portions of code, can include any appropriate media known or used in the art, including, but not limited to, volatile and non-volatile, removable, and non-removable media implemented in any method or technology for storage of information, such as computer readable instructions, data structures, program modules or other data, including RAM, ROM, EEPROM, flash memory or other memory technology, CD-ROM, digital versatile disk ("DVD") or other optical storage, magnetic cassettes, magnetic tape, magnetic disk storage or other magnetic storage devices, or any other medium which can be used to store the desired information and which can be accessed by a system device.

Figure 6:
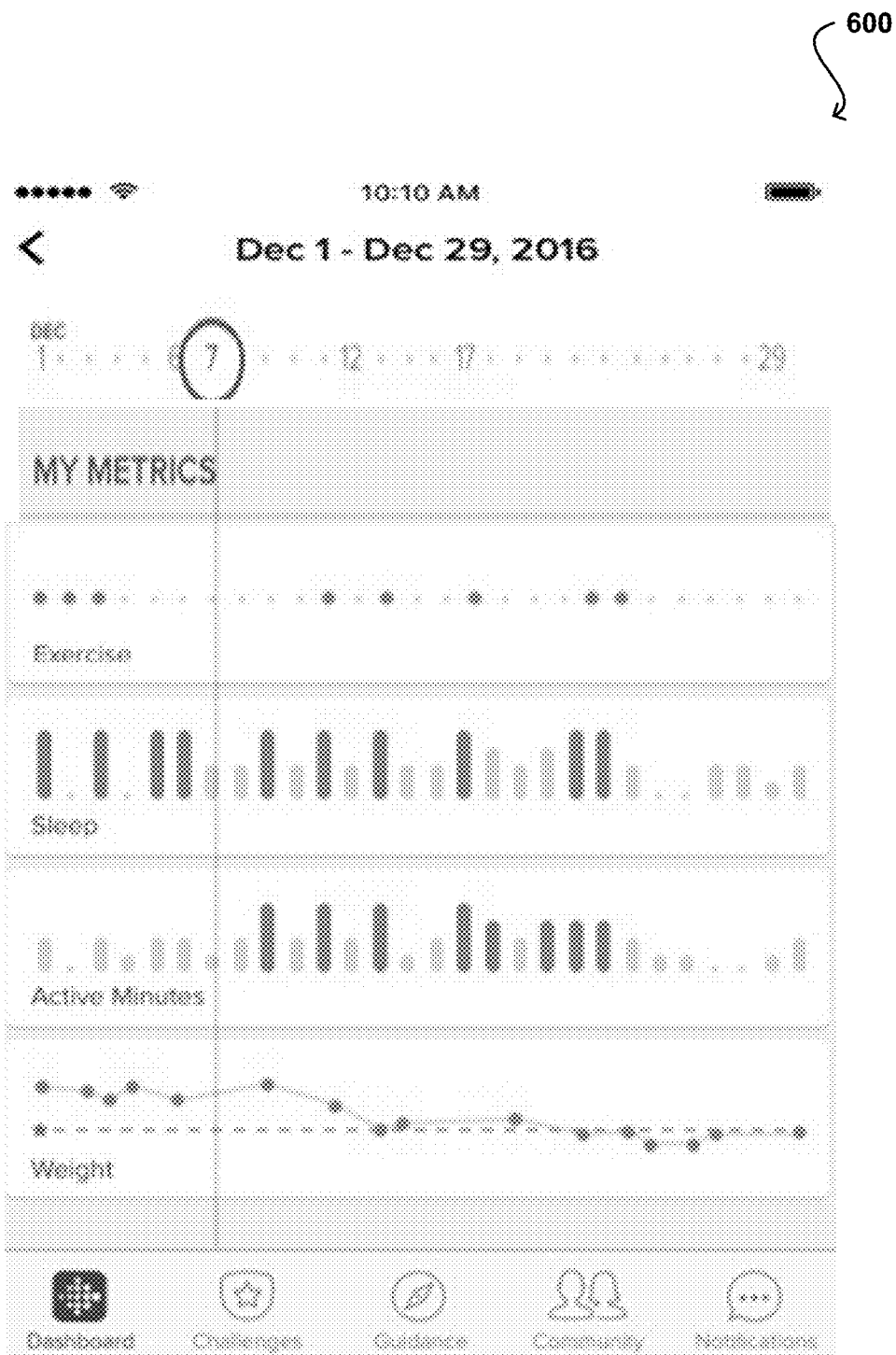
FIG. 6 illustrates an example user interface that can be utilized in accordance with various embodiments.

FIG. 6 illustrates an example user interface 600, such as might appear on a smartphone used in connection with a monitoring device, which can be utilized in accordance with various embodiments, wherein the various metrics discussed herein may be visually presented for the user, along with options to view other data such as current and/or predicted mental state statuses. Output, be it HR-related or otherwise, shown to the user, such as on the display of the monitoring device, may be a linear/bar graph or other such indicator. For example, interface 600 provides various metrics that are determined for a user and may be relevant to mental state. Information can be displayed such as relates to periods of exercise, weight fluctuation, sleep patterns, and the like. The information presented can also include mental state status and predictions as to a start of a depressed episode, among other such options. By way of further and ongoing output, the monitoring device 102 may provide prompts, reminders, instructions, guidance, and the like to encourage the user to develop habits which might result in an overall better mental state.

The date bar across the top of the interface 600 enables the user to zoom or focus on information pertaining to specific days. In some embodiments, the information can be presented in a circular or calendar format, etc. Circles or other graphical elements can show whichever day the user has scrubbed, allowing him or her to explore without having to show all of the day's numbers at once. On a touch-and-hold configuration, a vertical visual alignment assist ruler can appear and help with user navigation. A user can obtain information about trends potentially developing in the data and can then select certain information to obtain a second interface. Such an interface setup enables a user to quickly view information and see how that may have impacted various symptoms. The amount of information can be controlled in some aspects through scrolling, such as where a user can scroll up to hide the summary section, and further scrolling can scroll the metrics behind the header, among other such options.

Based on the disclosure and teachings provided herein, a person of ordinary skill in the art will appreciate other ways and/or methods to implement the various embodiments. The specification and drawings are, accordingly, to be regarded in an illustrative, rather than a restrictive, sense. It will, however, be evident that various modifications and changes may be made thereunto without departing from the broader spirit and scope of the invention as set forth in the claims.

What is claimed is:

1. A computer-implemented method, comprising:
   obtaining, using a non-invasive measurement system of a monitoring device worn by a user, physiological data including at least one of heart rate data, activity data, and sleep data;
   inputting the physiological data into a predictive model to identify one or more biomarkers relevant to a mental state of the user, the one or more biomarkers relating at least in part to one or more of a heart rate value, an activity time period, or a sleep time period;
   determining, using the one or more biomarkers, a mental state status for the user;
   obtaining gamification data for the user, using at least one gamification application executing on the monitoring device from a selected subset of games based at least in part on the mental state status, the at least one gamification application configured to measure at least one of impulsiveness, reaction time, and task switching ability;
   determining at least one variation in the one or more biomarkers based at least in part on the gamification data and a baseline established based at least in part on prior game performance of the user;
   updating the mental state status based at least in part on the at least one variation in the one or more biomarkers; and
   presenting, by a display on the monitoring device, the mental state status.

2. The computer-implemented method of claim 1, further comprising:
   providing a neural network, the neural network being at least one of a convolutional, long short-term memory, feedforward, recurrent, radial basis function, modular, and self-organizing network;
   training the neural network on a data set, the data set comprising information regarding at least one of physiological and mental health data; and
   applying the neural network to optimize the determination of the mental state status.

3. The computer-implemented method of claim 1, further comprising:
   calculating a probability score with regard to a likelihood that the user is at risk for a mental health disorder; and
   updating the mental state status based at least in part on the probability score.

4. The computer-implemented method of claim 1, further comprising:
   monitoring, by at least one predictive resting heart rate model, the physiological data over a future period of time;
   determining, during the future period of time, that the physiological data correlates with one of the one or more biomarkers; and
   updating the mental health state status based at least in part upon the physiological data correlating with one of the one or more biomarkers.

5. The computer-implemented method of claim 1, further comprising:
   obtaining additional data for the user for use in generating and updating the mental state status, the additional data including at least one of blood oxygen concentration level, body temperature, heart rate variability metrics, hormones level, sleep quality, activity and exercise level, step count, weight, height, time of the year, location, body mass index, or age information.

6. The computer-implemented method of claim 1, further comprising:
   obtaining historical data for the user, this historical data including at least one of physical health data and mental health data; and
   using the historical data, at least in part, to determine the mental state status.

7. The computer-implemented method of claim 1, wherein the monitoring device includes at least one of a smartwatch, a fitness band, a tracker ring, an earbud, smart clothing, a scale, a body composition analyzer, an electrodermal sensor, or smart bedding.

8. The computer-implemented method of claim 1, further comprising:
   obtaining at least the heart rate data using an optical sub-system including at least one optical emitter and at least one optical detector, the optical detector configured to detect light from the optical emitter that is not absorbed by the skin of the user.

9. The computer-implemented method of claim 1, further comprising:
   obtaining, at least in part, the physiological data using near-infrared spectroscopy with light of at least one wavelength between about 900 nm and about 1500 nm.

10. A computer-implemented method, comprising:
    obtaining historical information for a user;
    inputting the historical information into a predictive model;
    obtaining, using a non-invasive measurement system of a monitoring device worn by a user, physiological data including at least one of heart rate data, activity data, and sleep data;
    inputting the physiological data into the predictive model to identify one or more biomarkers relevant to a mental state of the user, the one or more biomarkers relating at least in part to one or more of a heart rate value, an activity time period, or a sleep time period;
    correlating, through the predictive model, patterns in the physiological data and historical information with the biomarkers;

determining, using the one or more biomarkers, a mental state status for the user;

obtaining gamification data for the user, using at least one gamification application executing on the monitoring device from a selected subset of games based at least in part on the mental state status, the at least one gamification application configured to measure at least one of impulsiveness, reaction time, and task switching ability;

determining at least one variation in the one or more biomarkers based at least in part on the gamification data and a baseline established based at least in part on prior game performance of the user;

updating the mental state status based at least in part on the at least one variation in the one or more biomarkers; and presenting, by a display on the monitoring device, the mental state status.

11. The computer-implemented method of claim 10, further comprising:

calculating a probability score with regard to a likelihood that the user is at risk for depressive disorder; and updating the mental state status based at least in part on the probability score.

12. The computer-implemented method of claim 10, further comprising:

obtaining the heart rate data using an optical photoplethysmogram ("PPG") sub-system of the monitoring device as worn by the user, the PPG sub-system operable to determine changes in absorption of the light in skin of the user.

13. The computer-implemented method of claim 12, further comprising:

obtaining motion data for the user using at least one motion sensor of the monitoring device; and filtering the heart rate data using the motion data.

14. The computer-implemented method of claim 12, further comprising:

obtaining additional data for the user; and using the additional data to train and update the predictive model, the additional health data including at least one of blood oxygen concentration level, heart rate variability metrics, body temperature, hormones level, sleep quality, activity and exercise level, weight, height, body mass index, or age information.

15. A monitoring device, comprising:

a display device;

a non-invasive measurement system;

at least one processor; and memory including instructions that, when executed by the at least one processor, cause the monitoring device to:

obtain, using the non-invasive measurement system, physiological data for a user, the physiological data including at least one of heart rate data, activity data, and sleep data;

input the physiological data into a predictive model to identify one or more biomarkers relevant to a mental state of the user, the one or more biomarkers relating at least in part to one or more of a heart rate value, an activity time period, or a sleep time period;

determine, using the one or more biomarkers, a mental state status for the user;

obtain gamification data for the user, using at least one gamification application executing on the monitoring device from a selected subset of games based at least in part on the mental state status, the at least one gamification application configured to measure at least one of impulsiveness, reaction time, and task switching ability;

determine at least one variation in the one or more biomarkers based at least in part on the gamification data and a baseline established based at least in part on prior game performance of the user;

update the mental state status based at least in part on the at least one variation in the one or more biomarkers; and provide, by the display, guidance information based at least in part on the mental state status.

16. The monitoring device of claim 15, wherein the instructions when executed further cause the system to:

receive indication of an occurrence of a potential depressed mental state; and update the mental state status based at least in part upon the indication.

17. The monitoring device of claim 15, wherein the instructions when executed further cause the system to:

monitor, by at least one predictive resting heart rate model, the physiological data over a future period of time;

determine, during the future period of time, an updated mental state status; and provide, by the display device, the updated mental state status.

18. The monitoring device of claim 15, wherein the instructions when executed further cause the system to:

obtain additional data for the user for use in generating and updating the mental state status, the additional health data including at least one of blood oxygen concentration level, body temperature, hormone level, sleep state, activity level, weight, body mass index, or age information.

19. The monitoring device of claim 15, wherein the instructions when executed further cause the system to:

obtain, at least in part, the physiological data using at least one of near-infrared or short-wave infrared spectroscopy with light of at least one wavelength between about 900 nm and about 1500 nm.

* * * * *